United States Patent
Wilson et al.

(10) Patent No.: US 10,940,002 B2
(45) Date of Patent: Mar. 9, 2021

(54) FORCE TRANSDUCTING INFLATABLE IMPLANT SYSTEM INCLUDING A DUAL FORCE ANNULAR TRANSDUCTION IMPLANT

(71) Applicant: Harmony Development Group, Inc., Cornelius, NC (US)

(72) Inventors: John Wilson, Cornelius, NC (US); Christopher Seguin, Norton, MA (US)

(73) Assignee: Harmony Development Group, Inc., Cornelius, NC (US)

( * ) Notice: Subject to any disclaimer, the term of this patent is extended or adjusted under 35 U.S.C. 154(b) by 198 days.

(21) Appl. No.: 16/021,985

(22) Filed: Jun. 28, 2018

(65) Prior Publication Data

US 2019/0000621 A1   Jan. 3, 2019

Related U.S. Application Data

(60) Provisional application No. 62/526,216, filed on Jun. 28, 2017.

(51) Int. Cl.
  *A61F 2/24*   (2006.01)
  *A61F 2/06*   (2013.01)

(52) U.S. Cl.
  CPC .......... *A61F 2/2445* (2013.01); *A61F 2/2448* (2013.01); *A61F 2002/068* (2013.01); *A61F 2210/0014* (2013.01); *A61F 2220/0008* (2013.01); *A61F 2220/0016* (2013.01); *A61F 2220/0025* (2013.01); *A61F 2230/0006* (2013.01); *A61F 2230/0008* (2013.01); *A61F 2230/0095* (2013.01);

(Continued)

(58) Field of Classification Search
  CPC ...... A61M 1/086; A61M 1/127; A61M 1/122; A61M 1/10; A61M 1/12; A61N 1/362; A61F 2/2445; A61F 2/2448
  See application file for complete search history.

(56) References Cited

U.S. PATENT DOCUMENTS

| | | |
|---|---|---|
| 6,406,422 B1 | 6/2002 | Landesberg |
| 6,827,682 B2 | 12/2004 | Bugge et al. |
| 7,435,257 B2 | 10/2008 | Lashinski et al. |

(Continued)

FOREIGN PATENT DOCUMENTS

| | | |
|---|---|---|
| CN | 105726072 A | 7/2016 |
| CN | 106214289 A | 12/2016 |

(Continued)

OTHER PUBLICATIONS

International Search Report and Written Opinion for International Application No. PCT/US19/20816 dated Jul. 9, 2019.

(Continued)

*Primary Examiner* — Jason-Dennis N Stewart
(74) *Attorney, Agent, or Firm* — Foley Hoag LLP; Stephen J. Kenny; Robert Piston

(57) ABSTRACT

An implant system for restoring and improving physiological intracardiac vortical flow in a human heart is provided including a dual force transducting annular implant comprising laterally extending struts transitioning into annular structural members for positioning on the atrial side of the valve annulus; an anchoring system comprising a therapeutic base plate assembly attachable to the apex of the heart; and a tether assembly comprising a tether connected between the implant and the therapeutic base plate assembly.

111 Claims, 17 Drawing Sheets

(52) U.S. Cl.
CPC ............... *A61F 2250/0001* (2013.01); *A61F 2250/0003* (2013.01); *A61F 2250/0006* (2013.01)

(56) References Cited

U.S. PATENT DOCUMENTS

| | | |
|---|---|---|
| 7,854,762 B2 | 12/2010 | Speziali et al. |
| 8,092,525 B2 | 1/2012 | Eliasen et al. |
| 8,778,017 B2 | 7/2014 | Eliasen et al. |
| 9,050,189 B2 | 6/2015 | Padala et al. |
| 9,078,660 B2 | 7/2015 | Boutillette et al. |
| 9,486,306 B2 | 11/2016 | Tegels et al. |
| 9,498,330 B2 | 11/2016 | Solem |
| 2003/0032855 A1 | 2/2003 | Shahinpoor |
| 2006/0058871 A1 | 3/2006 | Zakay et al. |
| 2006/0241745 A1 | 10/2006 | Solem |
| 2007/0198082 A1 | 8/2007 | Kapadia et al. |
| 2007/0265490 A1 | 11/2007 | Smith et al. |
| 2007/0270943 A1 | 11/2007 | Solem et al. |
| 2007/0282157 A1 | 12/2007 | Rottenberg et al. |
| 2008/0064917 A1 | 3/2008 | Bar et al. |
| 2008/0294251 A1 | 11/2008 | Annest et al. |
| 2008/0306328 A1 | 12/2008 | Ercolani et al. |
| 2009/0048668 A1 | 2/2009 | Wilson et al. |
| 2009/0131849 A1 | 5/2009 | Maurer et al. |
| 2009/0177028 A1 | 7/2009 | White |
| 2009/0254195 A1 | 10/2009 | Khairkhahan et al. |
| 2011/0022164 A1 | 1/2011 | Quinn et al. |
| 2011/0196483 A1 | 8/2011 | Forsell |
| 2011/0224655 A1 | 9/2011 | Asirvatham et al. |
| 2012/0143320 A1 | 6/2012 | Eliasen et al. |
| 2013/0030519 A1 | 1/2013 | Tran et al. |
| 2013/0172978 A1 | 7/2013 | Vidlund et al. |
| 2013/0325110 A1 | 12/2013 | Khalil et al. |
| 2014/0277404 A1 | 9/2014 | Wilson et al. |
| 2014/0309732 A1 | 10/2014 | Solem |
| 2014/0336751 A1 | 11/2014 | Kramer |
| 2014/0371789 A1 | 12/2014 | Hariton et al. |
| 2014/0371843 A1 | 12/2014 | Wilson et al. |
| 2014/0371846 A1 | 12/2014 | Wilson et al. |
| 2015/0073539 A1 | 3/2015 | Geiger et al. |
| 2015/0112429 A1 | 4/2015 | Khairkhahan et al. |
| 2015/0223934 A1 | 8/2015 | Vidlund et al. |
| 2015/0245934 A1 | 9/2015 | Lombardi et al. |
| 2016/0089234 A1 | 3/2016 | Gifford, III |
| 2016/0089237 A1 | 3/2016 | Wilson et al. |
| 2016/0113765 A1 | 4/2016 | Ganesan et al. |
| 2016/0199181 A1 | 7/2016 | Kramer |
| 2016/0242909 A1 | 8/2016 | Ketai et al. |
| 2016/0317290 A1 | 11/2016 | Chau et al. |
| 2017/0000935 A1 | 1/2017 | Vasilyev et al. |
| 2017/0136162 A1 | 5/2017 | van Dort et al. |
| 2017/0172737 A1 | 6/2017 | Kuetting et al. |
| 2018/0015141 A1 | 1/2018 | Jay et al. |
| 2018/0185145 A1 | 7/2018 | Wilson et al. |
| 2018/0318071 A1 | 11/2018 | Lozonschi et al. |
| 2018/0344461 A1 | 12/2018 | Wilson et al. |

FOREIGN PATENT DOCUMENTS

| | | |
|---|---|---|
| WO | WO-2012/130052 A1 | 10/2012 |
| WO | WO-2018/129312 A1 | 7/2018 |
| WO | WO-2018/129320 A1 | 7/2018 |
| WO | WO-2018/222894 A1 | 12/2018 |
| WO | WO-2019/006152 A1 | 1/2019 |
| WO | WO-2019/173385 A1 | 9/2019 |

OTHER PUBLICATIONS

International Search Report and Written Opinion of the International Searching Authority from parent application PCT/US2018/12578 dated Mar. 28, 2018.

International Search Report and Written Opinion for International Application No. PCT/US2018/034177 dated Jul. 20, 2018.

International Search Report and Written Opinion for International Application No. PCT/US2018/012586 dated Mar. 20, 2018.

International Search Report and Written Opinion for International Application No. PCT/US2018/034174 dated Jul. 27, 2018.

International Search Report and Written Opinion for International Application No. PCT/US2018/035427 dated Jul. 27, 2018.

International Search Report and Written Opinion for International Application No. PCT/US2018/040066 dated Sep. 12, 2018.

Extended European Search Report for EP Application No. 18736494.8 dated Aug. 28, 2020.

Extended European Search Report for EP Application No. 18736566.3 dated Aug. 20, 2020.

FORCE TRANSDUCTING INFLATABLE IMPLANT SYSTEM INCLUDING A DUAL FORCE ANNULAR TRANSDUCTION IMPLANT

CROSS-REFERENCE TO RELATED APPLICATIONS

This application claims the benefit under 35 USC § 119(e) of U.S. Provisional Application Ser. No. 62/526,216 filed Jun. 28, 2017, the entirety of which is hereby incorporated by reference.

TECHNICAL FIELD

The present disclosure relates generally to a force transducting, structurally stabilizing, vortex orienting or steering, and functionally ventricular assisting inflatable implant within a human heart for restoring and improving physiologic vortical intracardiac flow and utilizing the re-purposed native energy and force of the atrioventricular pressure gradient, via force transduction, to restore geometric elliptical shape, healthy proportion, and proper function to the atria, the ventricles and ventricular walls, and the valvular apparatus itself.

SUMMARY

An implant system for restoring and improving physiological vortical intracardiac flow, reducing or impairing atrioventricular pressure gradient loss or regurgitation, improving or restoring ventricular elliptical geometry and function, and providing ventricular functional and structural support within an impaired human heart is provided including both a dual force transducting annular implant, comprising laterally extending struts transitioning into annular structural components for positioning and buttressing and/or anchoring on the atrial side of the valve annulus, and a vortex flow directing implant comprising an inflatable 'member' or bladder; an anchoring system comprising a therapeutic base plate assembly attachable to the heart; and a conduit tether or shaft assembly comprising a shaft connected between the implant and the therapeutic base plate assembly.

In some embodiments, the dual force transducting annular implant is fixed at the inflow side of a shaft in the atrium and anchored to the hearts apex. In some embodiments, the dual force transducting annular structural components on the inflow side are in contact with the annular structure. In some embodiments, the dual force transducting annular structural components stabilize the device, center the device, and mechanically connect the valve plane with the apex of the heart and thus transduct or move an increased reparative force to the annulus, the structures of the heart, the ventricles, and the ventricular walls, and aid in the geometric re-shaping of the impacted ventricle, the reverse or positive remodeling of the ventricles, the reparative strengthening of the ventricular walls, and assist the ventricle in systolic ventricular ejection thus functioning as a passive ventricular assist. By adding a constant amount of cinching force and supporting structure between the valve plane and the apex by tethering or anchoring the annulus to the apex of the heart, this becomes a passive ejection assist to aid ventricular ejection and cardiac function. In some embodiments, the annular structural components are fixed in location, in contact with, and attached to the annular structure, and/or shape and/or re-shape the valve annulus. In some embodiments, the laterally extending struts are nitinol or elastic and/or spring-based to absorb, collect, and store, energy and force in one cardiac cycle and then release, discharge, and transfer this energy and force during the subsequent cycle into the endocardium, myocardium, and epicardium via an attached apical base plate. In some embodiments, the laterally extending struts are elastic, nitinol, spring-like, and/or another expandable material designed to absorb energy and force in diastole, return energy and force in systole, and "launch" native cardiac energy and force.

In some embodiments, the dual force transducting annular implant has one or more contact points in the heart. In some embodiments, the annular structural components are positioned on the inflow side of the valve. In some embodiments, the annular structural members are nitinol, elastic, expandable, and/or rigid. In some embodiments, the annular structural members have a covering to promote endothelization.

In some embodiments, the system may further include a vortex flow directing implant that further employs the concept of force transduction and vortical flow direction. Force transduction is defined as the intentional movement and re-purposing of native energy and force from one area of the heart to another area of the heart. The movement of this energy and force can be delivered as a restoring therapy to components of the heart that have been adversely effected by pathology or cardiac insult. The design and shape of the vortex flow directing implant also enables vectoring and/or directional change of inflowing blood thereby enabling the restoration and enhancement of ventricular vortex formation. Ventricular vortex formation is critical to healthy physiologic intracardiac blood flow and overall human circulatory health. By placing the vortex flow directing implant atrioventricularly, the 'member' captures the forces applied by the valve leaflets and valvulo-ventricular structures driven by the atrioventricular pressure gradient. The atrioventricular pressure gradient is the source of the energy and force which is captured by the 'member' and transferred via the tether or shaft, and delivered to the ventricles, its structures, and the ventricular free walls via the ball jointed apical base plate and/or a fixed base plate. This delivery of re-purposed energy and force creates a restoring, reshaping, and repairing ventricular therapy by re-creating, replicating, and delivering the natural valvulo-ventricular interaction the native heart has lost due to pathology, cardiac event or insult, or structural failure. In some embodiments, the dual force transducting annular implant is detachable from the vortex flow directing implant. In some embodiments, the annular structural components control the shape of the atrium around the valve annulus. In some embodiments, the annular structural components may control the shape of the native annulus of the heart.

In some embodiments, the dual force transducting annular implant structural component defines a "D"-shape and/or saddle shape and/or circular and/or oval shape. In some embodiments, the vortex flow directing implant, acting as a force transducting implant itself by allowing the atrioventricular pressure gradient to act on the exposed surface area of the implant thereby capturing and/or harnessing its energy and force, is fluid-expanding and/or self-forming. In some embodiments, both the dual force transducting annular implant and the vortex flow directing implant, both acting as force transducting implants, and when attached to a shaft and tethered to an apical base plate then function or act as an additional or prosthetic 'papillary muscle' transducting and/or moving atrioventricular pressure gradient energy & force to the ventricular walls, structures, and into the ventricle itself.

BRIEF DESCRIPTION OF THE DRAWINGS

The objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

DETAILED DESCRIPTION

Figures 1, 2:
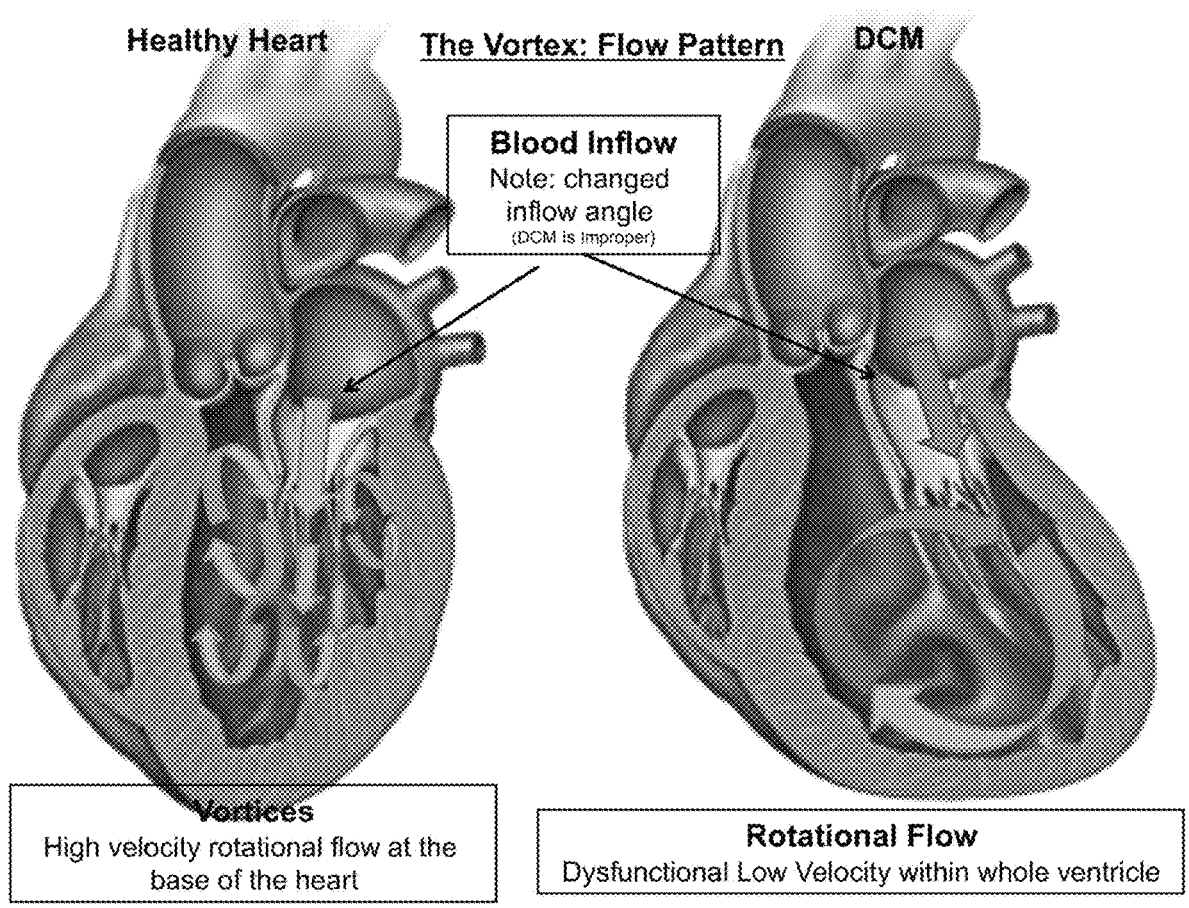
FIG. 1 is a diagram illustrating the vortex flow pattern of a healthy human heart.
FIG. 2 is a diagram illustrating the dysfunctional vortex flow pattern of a human heart with pathology.

One of the features of the healthy human heart function is proper physiological vortical intracardiac flow. During the ventricular systolic cycle, considerable forces are naturally generated and this energy and force is exerted on the closed or sealed atrioventricular valve. This filling phase occurs naturally and is powered, inside the human heart by a pressure gradient called the 'atrioventricular pressure gradient'. The atrioventricular pressure gradient is defined as a pressure difference (or a pressure differential) that produces or generates an energy and a force within the chambers of the heart, this being naturally occurring, naturally initiated, and naturally applied. When the pressure in the atrium is greater than the pressure in the ventricle, also called the 'diastolic' phase or diastole, blood flows from the higher-pressure atrium into the lower pressure ventricle, causing the atrioventricular valve leaflets to open thereby allowing blood to pass. During the ejection or pumping phase, also called the 'systolic' phase or systole, the pressure in the atrium is exceeded by the pressure in the ventricle thereby generating a pressure differential creating an energy and force which, in turn, pushes up, onto, and against the valve leaflets and causes or effects the valve leaflets to close and seal off the ventricular chamber from the atrial chamber. The atrioventricular pressure gradient, then, is the sealing energy and force required to close the valve. The blood is then ejected from and out of the ventricle, leaving the heart through the aortic valve, and out to the human body. The ventricle, contracts toward the end of the diastolic cycle and beginning the systolic cycle. This contraction initiates the atrioventricular pressure gradient, mentioned above, that initiates this pressure, or energy and force, which 'closes the valve leaflets', which then seals the ventricular chamber closed. In the remaining systolic cycle, blood, under high pressure, is then ejected via muscular force aided by the healthy ventricular vortex (formed in the diastolic cycle) to complete the hemodynamic cardiac output for that particular cycle. This cardiac cycle continues throughout the human lifecycle. When the valve leaflets seal properly, the atrioventricular pressure gradient forces close the valve leaflets and maintains and provides a strong ventricular structure to contain and utilize the atrioventricular pressure gradient for hemodynamic ejection and structural heart health. The papillary muscles, attached to the chordae tendineae, exercise and pull on the ventricle and ventricular walls thus maintaining the healthy ventricular shape, the healthy ventricular free wall, and healthy ventricular function (this is natural 'force transduction'). These native forces are delivered via the chordae tendinae and papillary muscles into the ventricular wall. This resulting valvulo-ventricular interaction keeps the ventricular structure healthy and provides the ventricle with structural support to maintain the proper elliptical ventricular geometry and functional shape. Geometric stability and ventricular function is maintained by imparting energy & force into the ventricular walls to maintain the healthy ventricle, to maintain the structures of the ventricle, to maintain the structures of the valve, and provides for dynamic proper hemodynamic ejection. During ventricular diastole, the ventricular pressure rapidly decreases. The valve opens and blood rushes from the atrium into the ventricle through the valve orifice. The valve leaflets function as a steering plane or a vectoring lever, directing ventricular flow at an angle or vector to develop and create an initial spin as illustrated in FIG. 1. Such angle may be due to the asymmetry of the valve leaflets and/or to the different shapes and sizes of the leaflets. A vortex progression results.

It is believed that the inflowing blood leaving the leaflets at angle or vector is critical in the formation of ventricular vortex. The initial hemodynamic spin then begins, in which the inflowing blood, engaged by the atrioventricular pressure gradient, then engages that initial spin such that a vortex is created downstream. As the blood leaves the leaflets at vector, due to boundary layer conditions, initial spin begins in which the inflowing blood downstream is engaged (by the pressure differential or gradient) such that a vortex is created in the healthy elliptically shaped ventricle. The resulting high velocity rotational flow, now a reservoir of kinetic energy within the ventricle is believed significant to proper blood flow velocity and volume through and out of the heart. Poor or altered vector and/or ventricular dysfunction can alter the formation of the ventricular vortex and thus impact negatively intracardiac flow and output.

Figure 3:
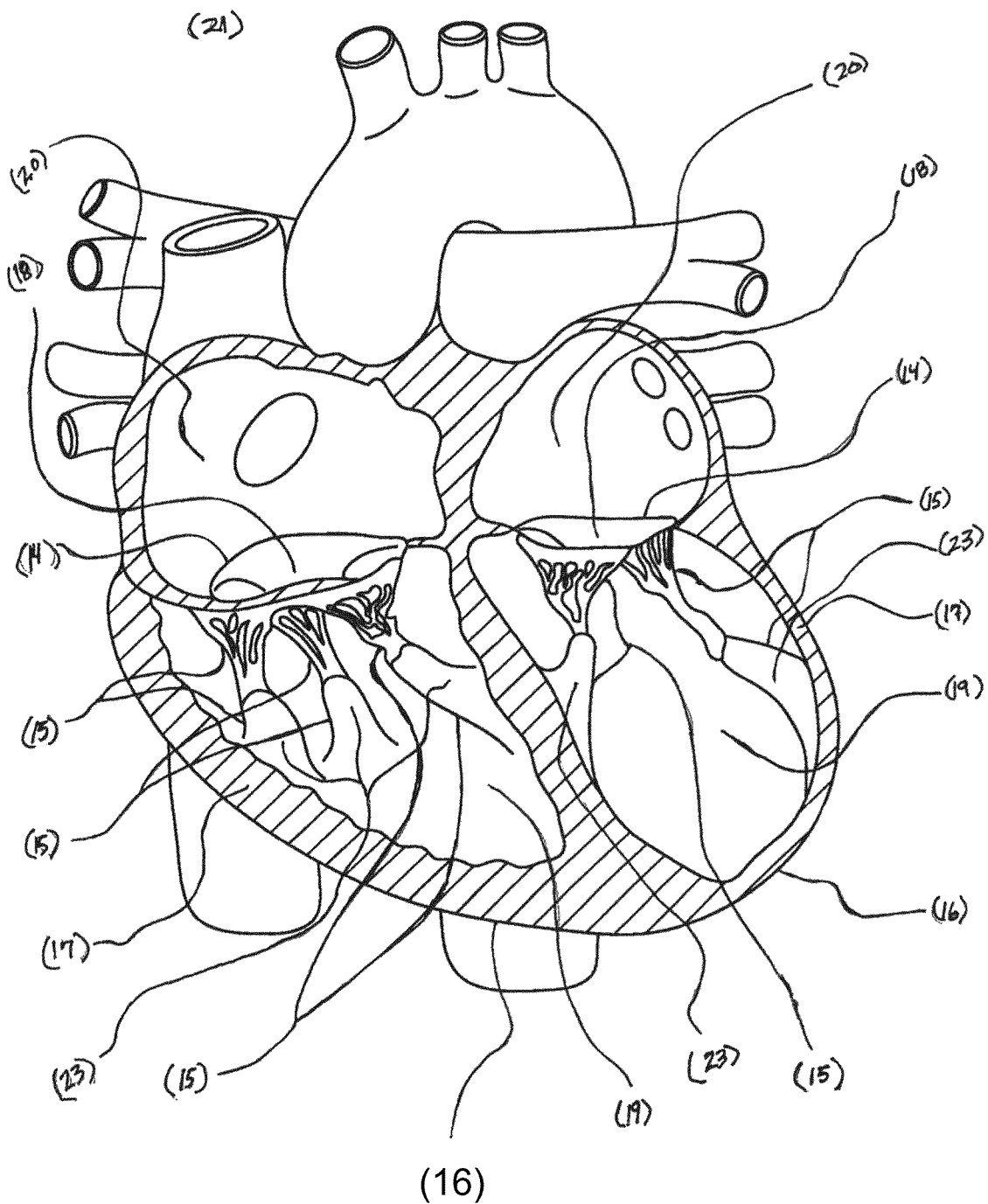
FIG. 3 is a diagram illustrating the structures of a human heart.
Figure 4:
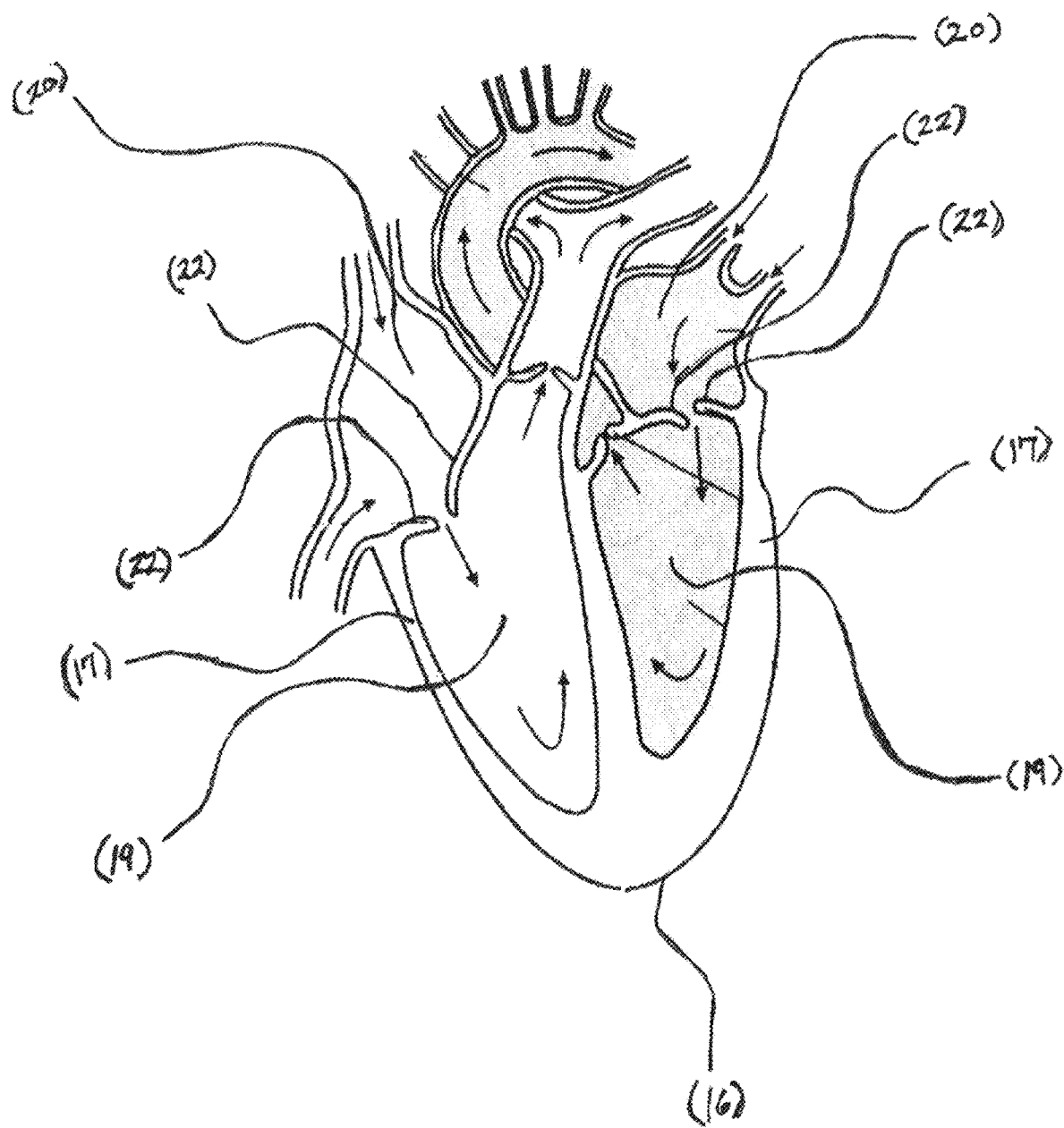
FIG. 4 is a diagram illustrating the vortex flow pattern of a healthy human heart.
Figure 5:
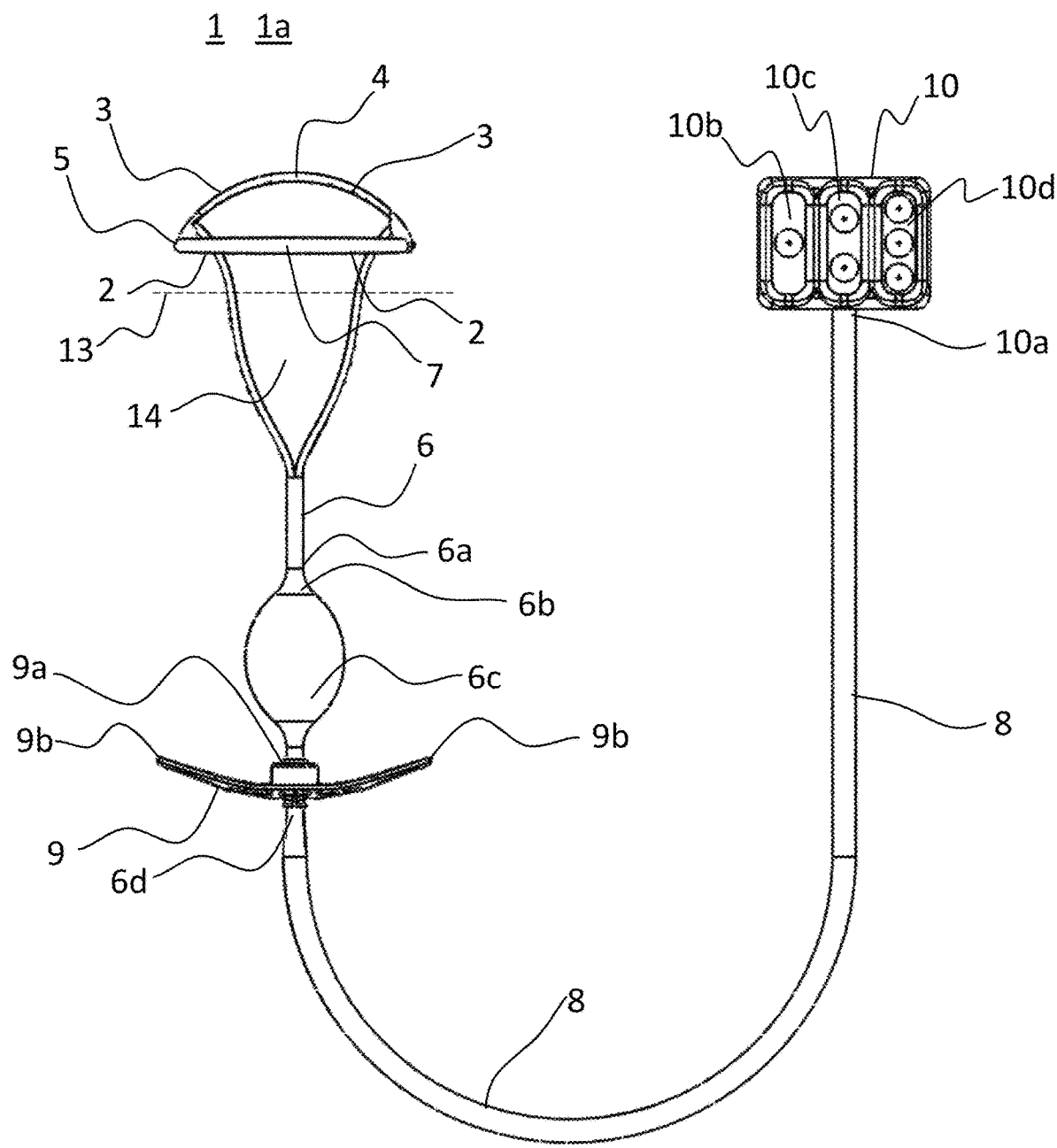
FIG. 5 is a side view of an implant system in accordance with an exemplary embodiment of the disclosed subject matter.
Figure 6:
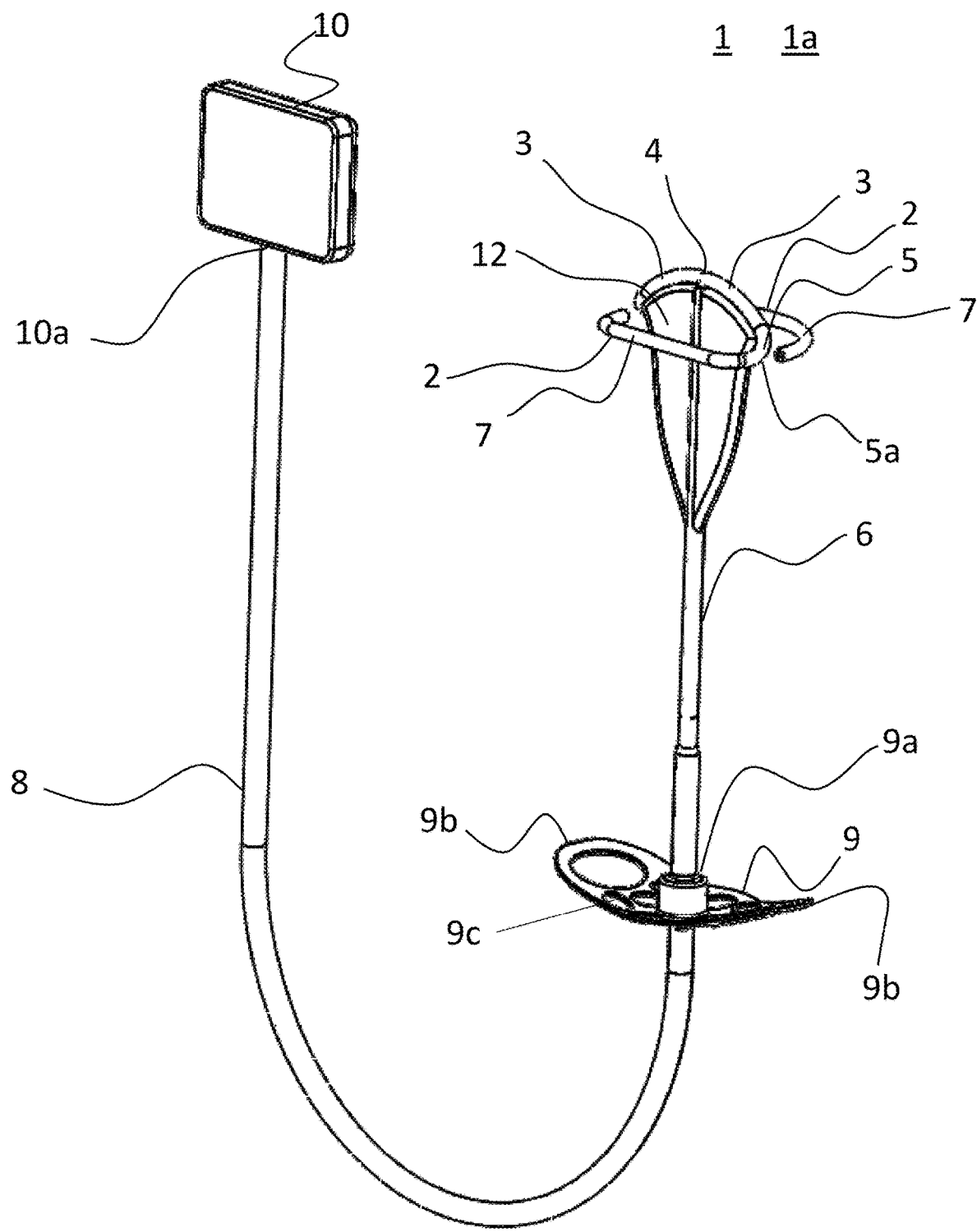
FIG. 6 is a perspective view of the implant system of FIG. 5 in accordance with an exemplary embodiment of the disclosed subject matter.
Figure 7:
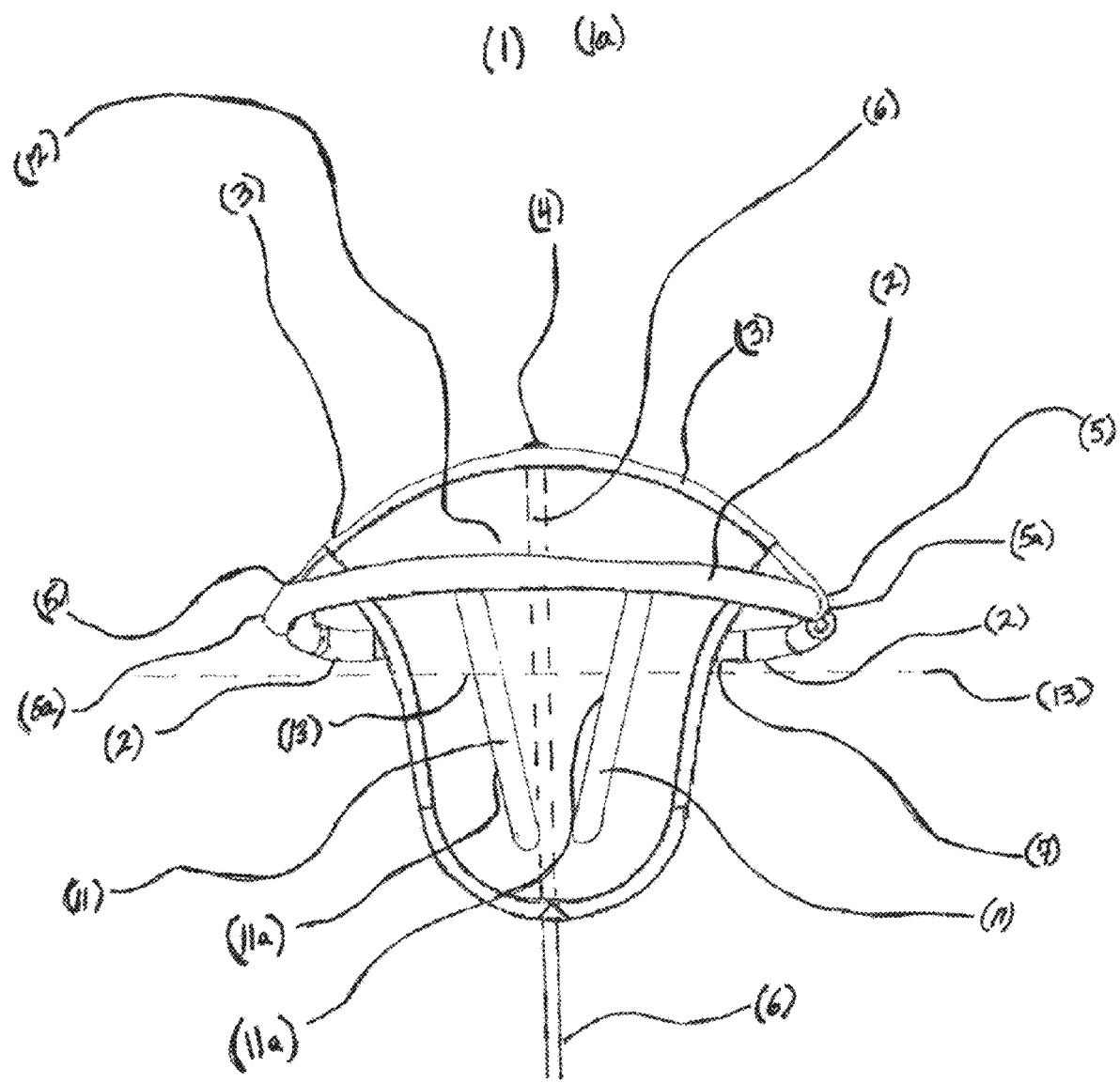
FIG. 7 is an enlarged side view of a vortex flow directing implant with the attached dual force transducting annular implant in accordance with an exemplary embodiment of the disclosed subject matter.
Figure 8:
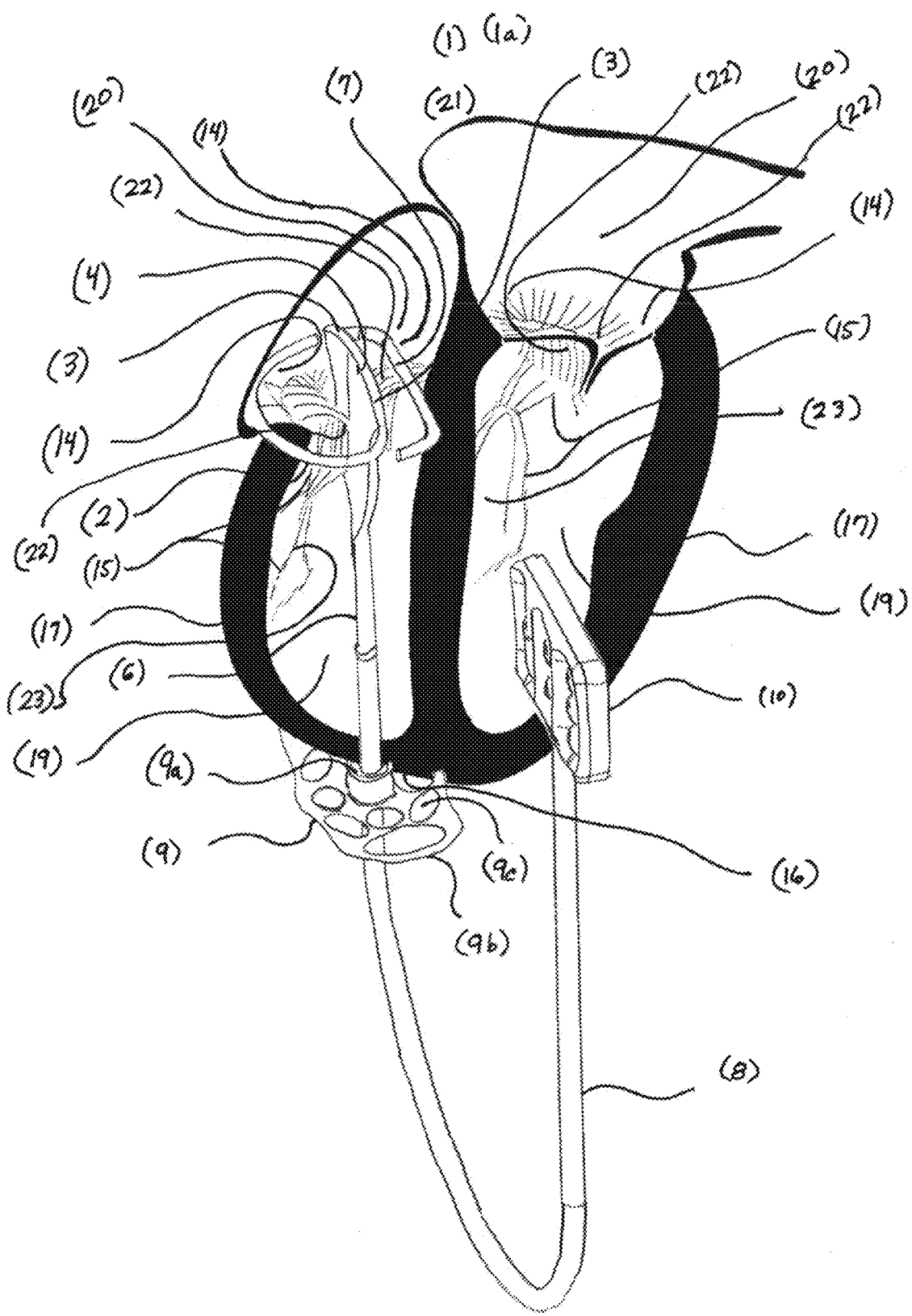
FIG. 8 is a partial cutaway view of an implant system in accordance with an exemplary embodiment of the disclosed subject matter, as positioned in the human heart.

FIG. 2 illustrates that under certain conditions, such as dilated cardiomyopathy (DCM) in which the heart becomes enlarged, the vortex and vortical flow patterns fail to properly form, geometric stability is compromised, the papillary muscles displace, and the elliptical shape is lost and, subsequently, the ventricle is unable to pump blood efficiently. Such conditions are marked by a low velocity flow, cascading symptoms such as regurgitation and annular distortion, and poor cardiac output in which the vortices are abnormal or absent and geometric distortion is present. Structures of the human heart 21 are illustrated in FIGS. 3 and 4 and referenced below.

In accordance with the disclosed subject matter, an implant system 1 is illustrated in FIGS. 5-13. Implant system 1 may include, e.g., a dual force transduction annular implant 1a, with a vortex flow directing 'member' 12, or a dual force transduction annular implant 1b, without a vortex flow directing 'member' 12, that is positioned within the FIG. 3 human heart 21 and connects, cinches and ties the annulus 14 of the atrioventricular valve and it's subvalvular apparatus 15 to the apex 16 and/or the ventricular wall 17 of the human heart via a conduit tether or shaft 6 and then with elastic spring-like property or spring-recoil based connection or strut 3 to aid in ventricular action and function by absorbing and loading the energy and force of the atrioventricular pressure gradient during one phase, diastole, and subsequently releasing it during the next phase, systole, of the cardiac cycle; absorbing and loading in one phase and releasing in the subsequent phase. This natively generated energy and force, the atrioventricular pressure gradient, is also captured, harnessed, and the transferred by the vortex flow directing 'member' 12 via the tether or shaft 6 to the base plate 9 and then through that base plate 9b into the ventricle 17, its structures, and the ventricular free wall 19.

The dual force transducting annular implant 1a, 1b is designed to load energy and force in the diastolic cycle and release the loaded energy and force in the following systolic cycle, effectively becoming a spring/recoil based assisting device for an impaired ventricle. The dual force transducting annular implant 1a therapeutically re-directs and re-purposes this cardiac energy and force via a nitinol, elastic, or spring recoil-based strut 3 in addition to the native atrioventricular pressure gradient energy and force and pressure forces of the structures of the FIG. 3 heart 21, hemodynamic forces, muscular action, muscular forces, the valve 18, valvular and subvalvular structures 15, and rotational energy to effect ventricular systolic and/or diastolic function, geometric reshaping of the ventricle 19, structural integrity of the ventricular free wall 17, and ventricular systolic function, acting as a ventricular assist, while at the same time functioning as a support for the annulus 14 and/or functioning as a reshaping band, framework, or structure. The device in its entirety functions, secondarily, as a shoring-up structural support framework for the weakened or impaired human heart.

Figure 13:
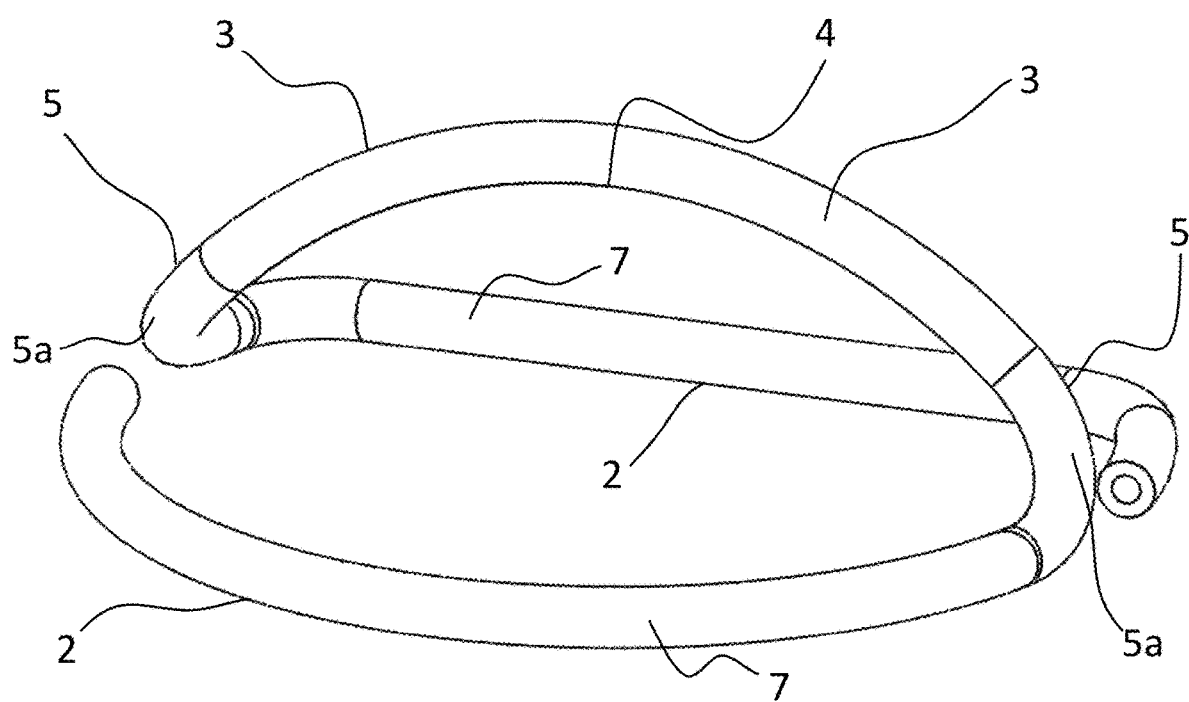
FIG. 13 is an enlarged perspective view of a dual force transducting annular implant in accordance with a second exemplary embodiment of the disclosed subject matter.
Figure 14:
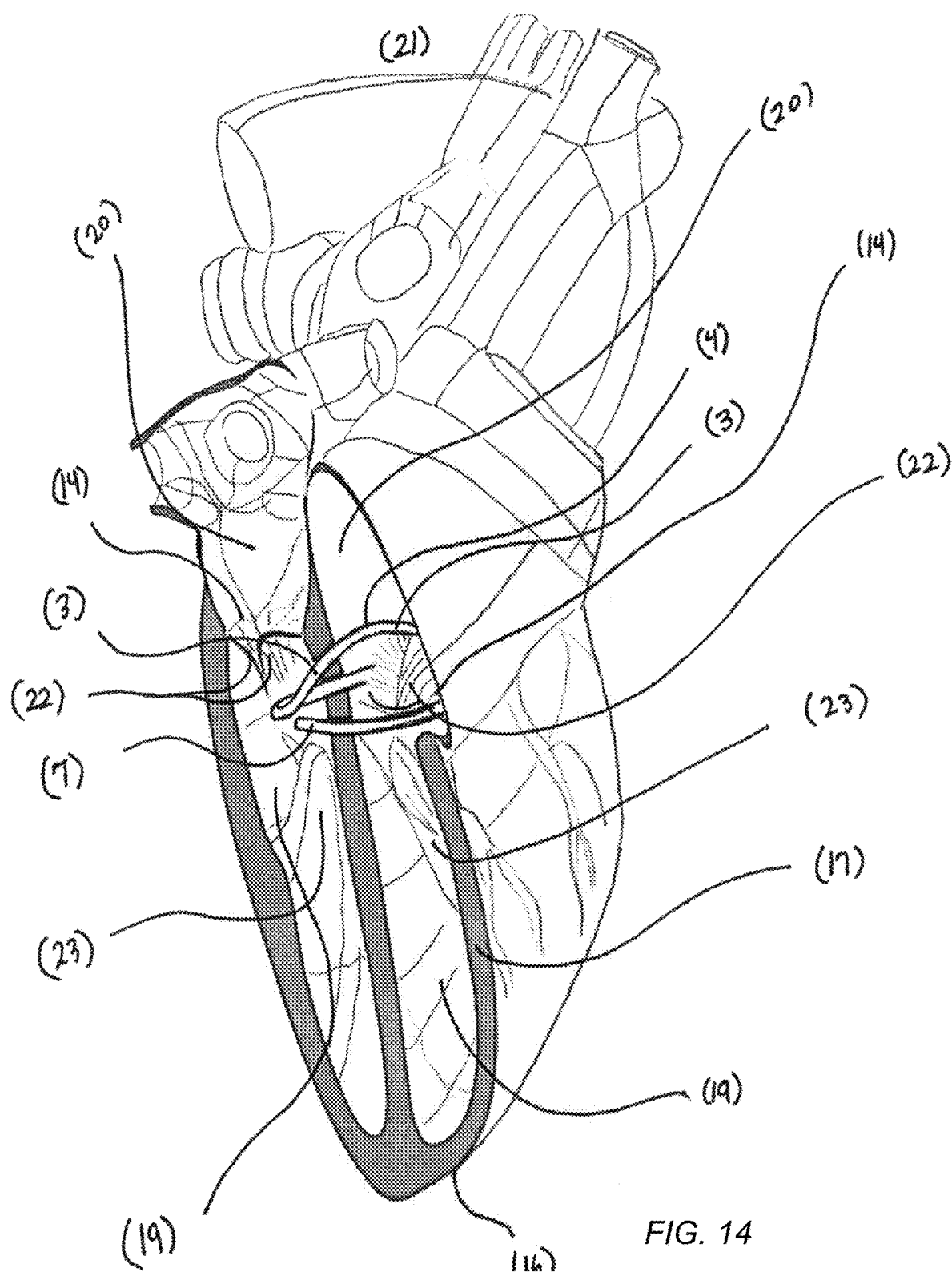
FIG. 14 is a partial cutaway view of an implant system in accordance with a second exemplary embodiment of the disclosed subject matter, as positioned in the human heart.
Figure 16:
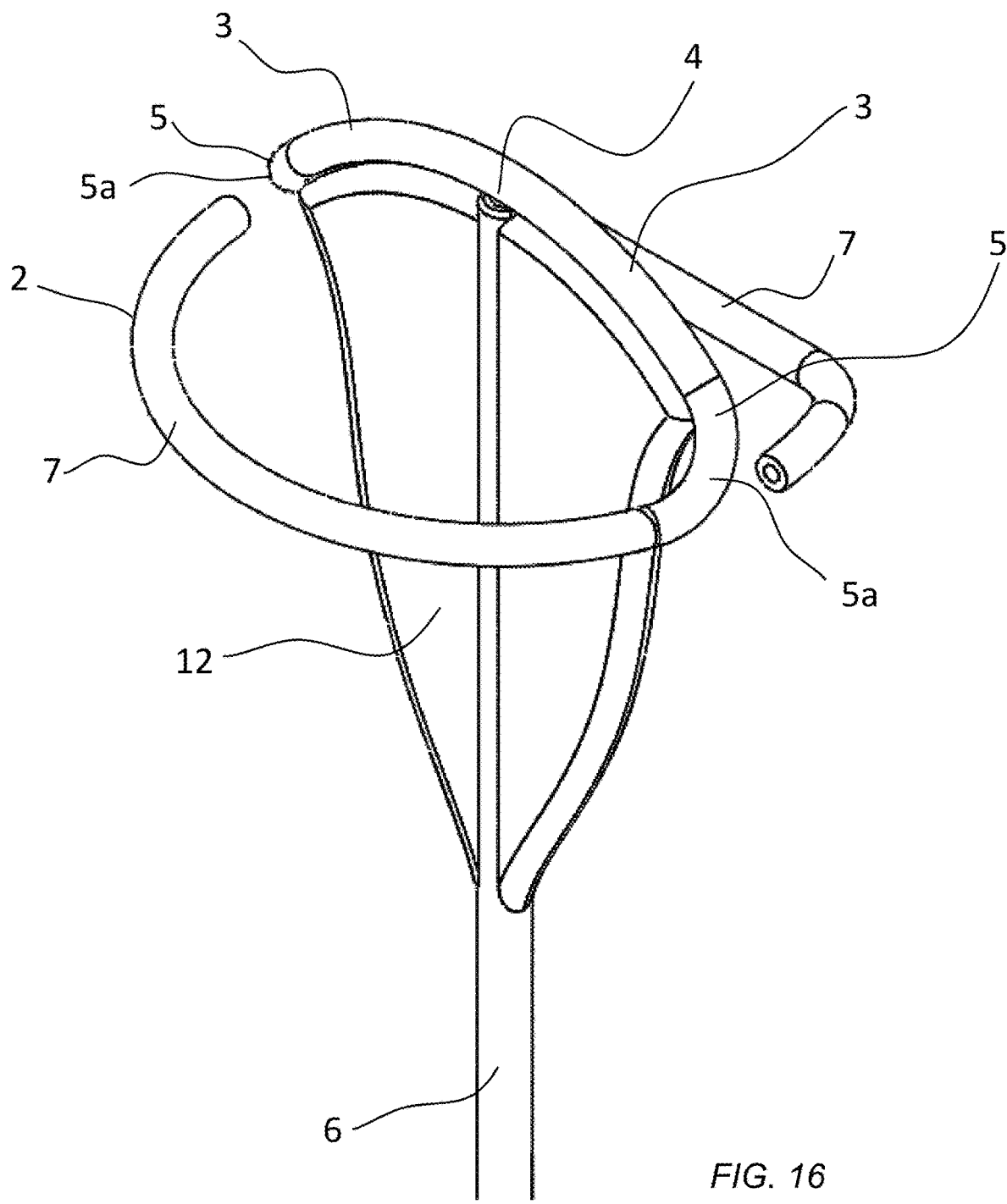
FIG. 16 is an enlarged perspective view of the distal portion of the dual force transducting annular implant system of FIG. 5. in accordance with an exemplary embodiment of the disclosed subject matter.
Figure 17:
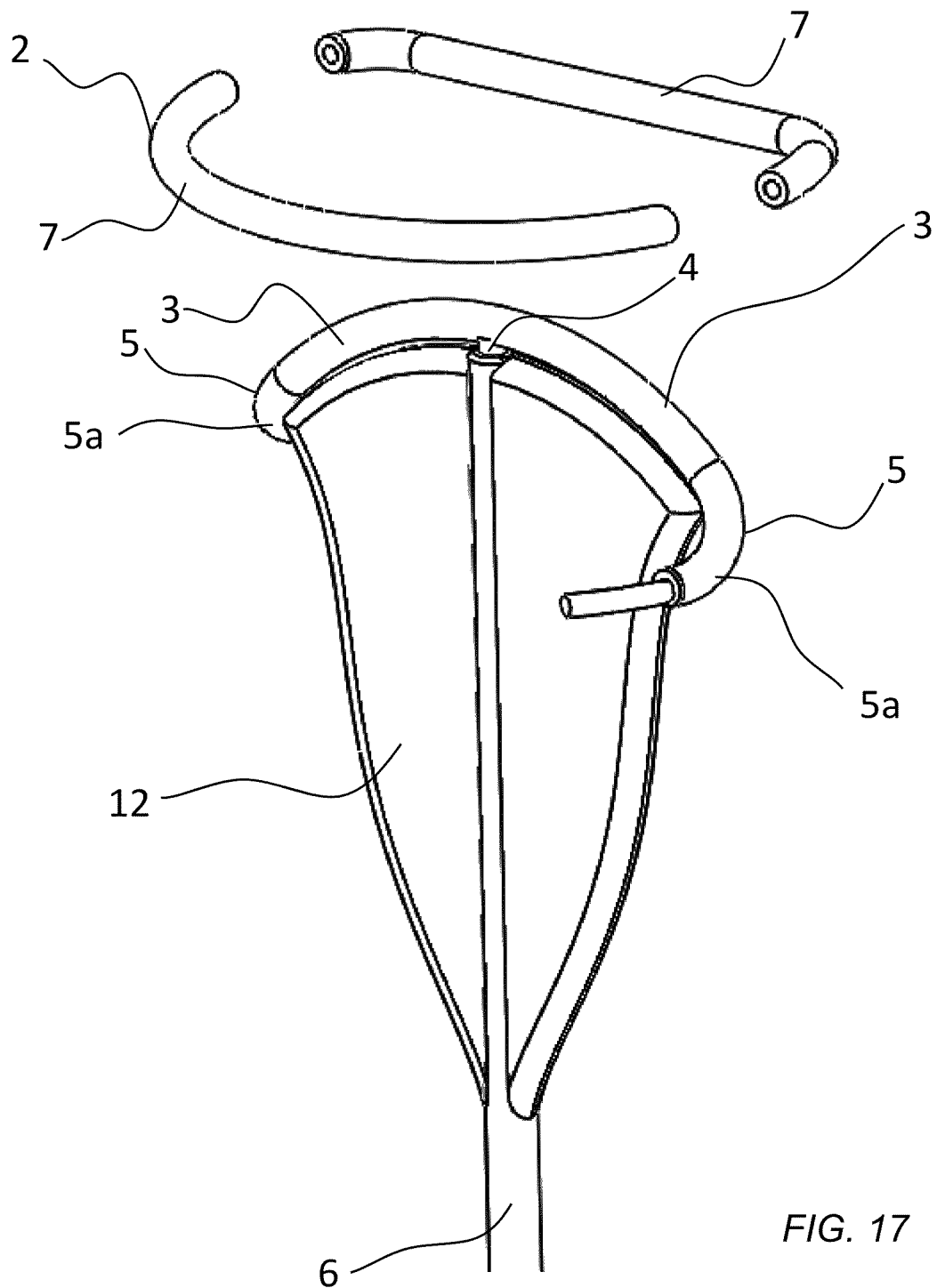
FIG. 17 is an enlarged perspective view of the distal portion of the dual force transducting annular implant system of FIG. 16 with the annular ring portion detached, in accordance with an exemplary embodiment of the disclosed subject matter.
Figure 18:
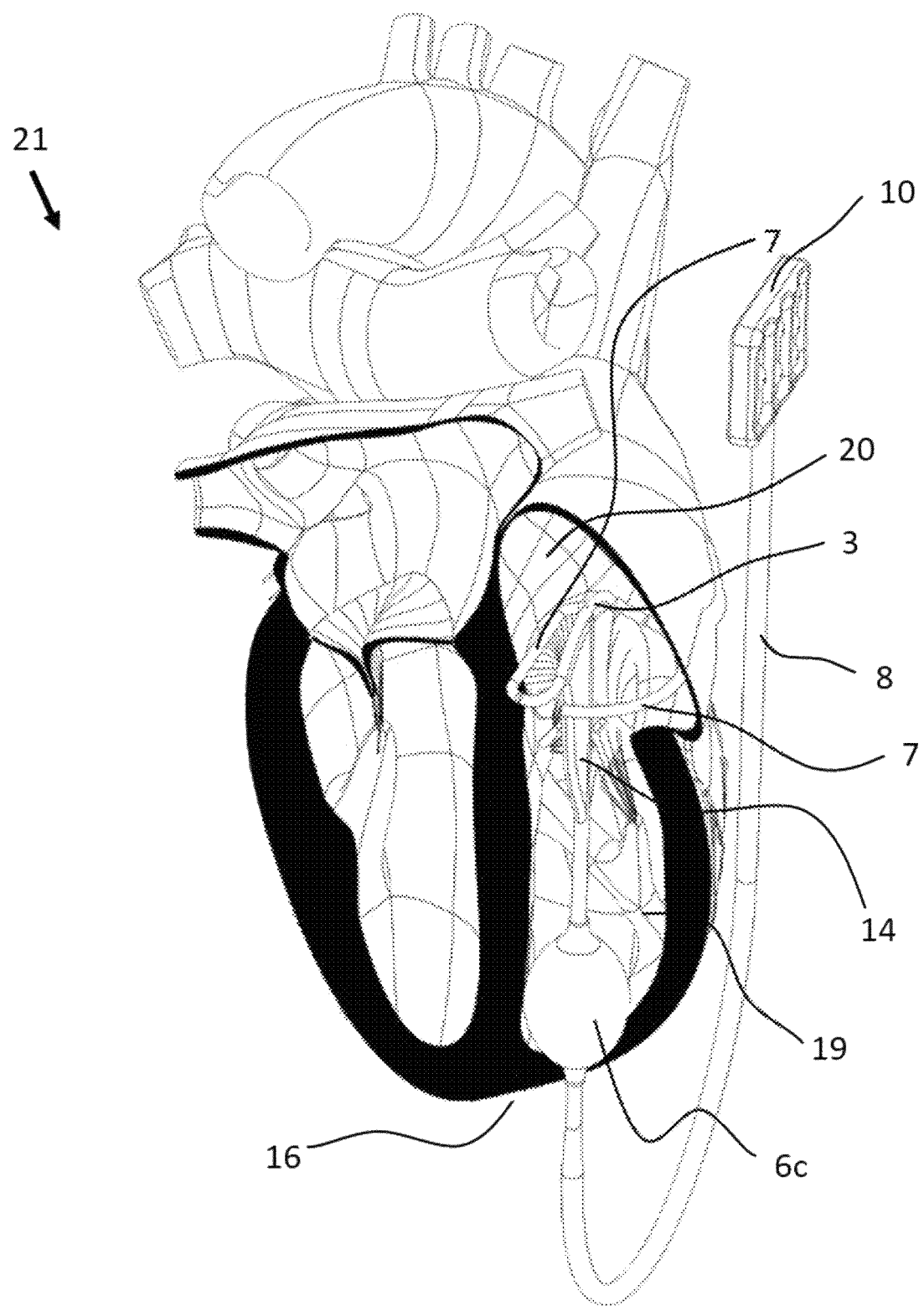
FIG. 18 is a partial cutaway view of an implant system in accordance with an exemplary embodiment of the disclosed subject matter, as positioned in the human heart.
Figure 19:
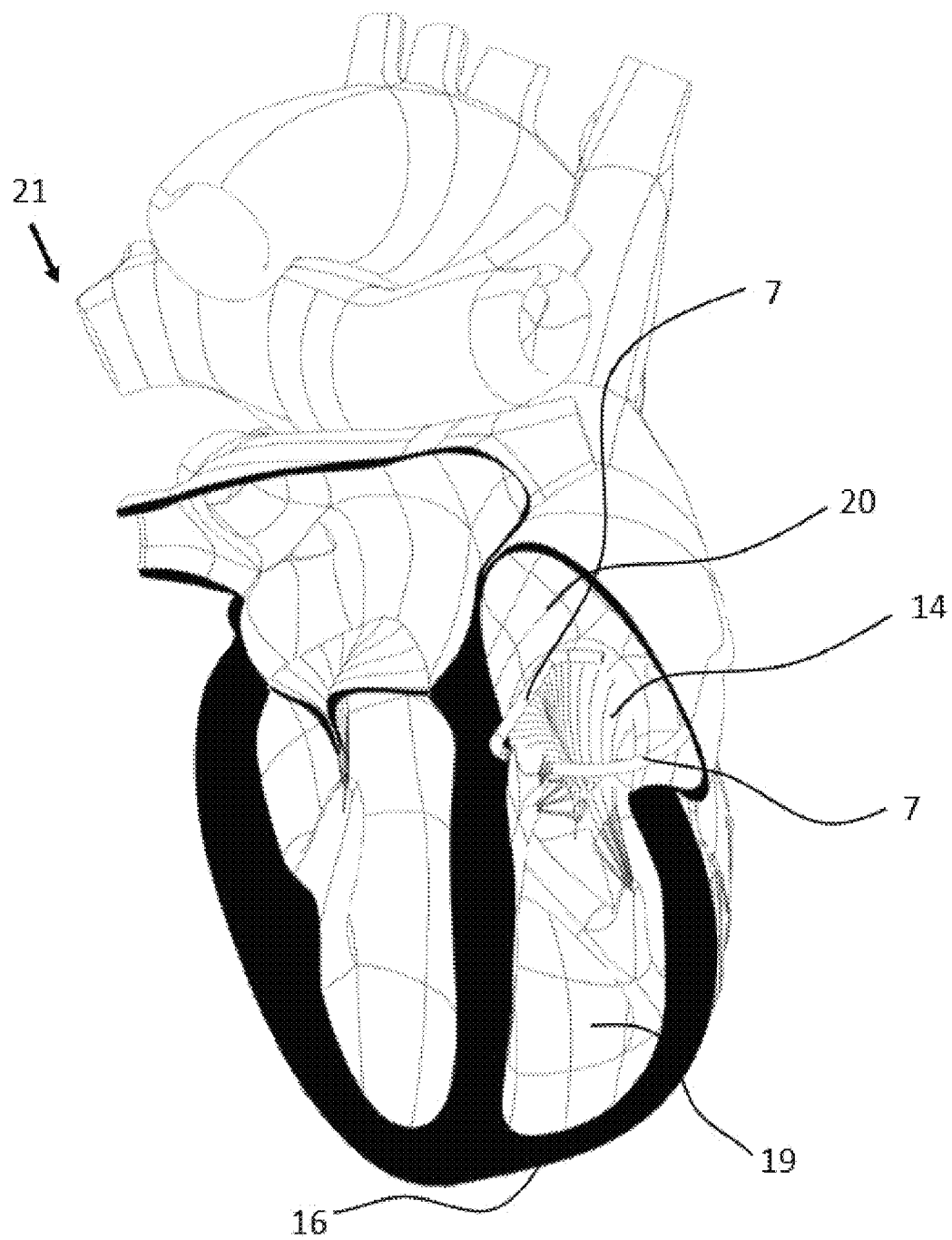
FIG. 19 is a partial cutaway view of the implant system of FIG. 18, as positioned in the human heart, with the annular ring remaining and the remainder of the implant system removed.

The implant 1a, 1b includes a self-expanding frame 2, fabricated of nitinol or any self-expanding or memory shape material. FIG. 13 Strut 3 (or a plurality of struts) extend away from the central fixation point 4, and include deployed ribs 5 on either side. The ribs 5 transition at a transition point 5a, also serving as a detaching point or an elbow, into a D-Frame or circular shaped, self-expanding, self-forming or shaped, annular ring or support 7. As illustrated in FIGS. 16 and 17, annular ring or support 7 is detachable from the ribs 5 at detaching point 5a. As shown in FIG. 18, the annular ring 7 is positioned adjacent to the annulus 14. As shown in FIG. 19, the ring 7 may be detached from the strut 3, and the implant system 1a, 1b removed. The remaining annular ring 7 conforms to an anatomical topography, e.g., annulus 14. (see, e.g., FIGS. 18,19.) Situated or placed above, in proximity to, or at the atrial annular ring 14, on the inflow side of the valve 18, the implant 1a, 1b has a strut 3, or struts, that are fixed at fixation point 4 onto the distal end of a multi lumen force transducting fixed tether or shaft 6, transitioning into an inner fixed tether or shaft 6a and an outer axially moving tether or shaft 6b. The outer axially moving tether or shaft 6b includes an integrated inflatable axially adjusting balloon 6c, with the whole of the tether or shaft transitioning at joint 6d into a multi lumen tube 8 after exiting the apex 16 of the heart 21, in this embodiment. The tether or shaft 6, in its entirety, is fixed to the apex 16 of the heart 21 by a base plate 9 and may include a ball joint 9a, to normalize and evenly transfer force into the ventricular wall 17. The multi-lumen tubing 8 is connected to a control unit 10 that adjusts the device performance via a fluid communicating system when connected, via the connection point 10a to the multi lumen tube 8. Control unit 10 is further illustrated in FIG. 10.

Dual Force Transduction Implant 1a

According to a first embodiment, the dual force transduction annular implant 1a has multiple functions. A first function of dual force transduction annular implant 1a is to mechanically re-connect the valve 18 and the subvalvular structures 15 with (or to) the ventricular walls 17 in this embodiment, by cinching the annulus 14 to the heart's apex 16, and to deploy a nitinol, elastic, spring recoil-based, and/or externally added energy loading strut 3 to aid in ventricular action and function, during the cardiac cycle, by absorbing and loading the energy and force of the atrioventricular pressure gradient during one phase, diastole, and subsequently releasing it during the next phase, systole; absorbing and loading in one phase releasing in the subsequent phase. It additionally captures, harnesses, and transducts native energy and force being generated by the FIG. 3 human heart 21 as a whole, e.g., its muscular force, hemodynamic energy, and rotational energy, on the atrial 20 side of the valve 18, and specifically within the valve 18 and to transduct or move this energy and force via the shaft 6 to the therapeutic base plate 9 to be therapeutically delivered into the ventricular structures 15, 17, 19 and ventricular free walls 17.

A second function of the dual force transduction annular implant 1a is to restore healthy intracardiac vortical blood flow. The vortex flow directing implant 'member' 12, placed and fixed in the valve orifice, purposed to intercept, steer, direct, vector, re-vector, and channel atrial inflow thereby passing blood onto and over the valve leaflets and into the ventricle 19. In positioning and fixing the vortex flow directing 'member' in such a way, the angle or vector at which the blood moves onto and off of the valves leaflets may be influenced, altered, or changed by increasing or decreasing the girth or inflation of the vortex flow directing 'member'. This ability of the implant 1, 1a to change the vector creates a tool for the initiating, enhancing, restoring, and/or assisting of the formation of ventricular vortex under visualization such as echocardiography. Positioned atrioventricularly, the vortex flow directing FIG. 9 implant 12 intercepts and re-vectors blood by channeling the atrial flow via and into the flow directing ribs 11 with the transition exiting surfaces 11 a being inside the ventricle. The vortex flow directing implant is the primary instrument of force transduction as well. The exposed area of the vortex flow directing implant 12 is acted on by the valve's leaflets capturing, harnessing, and then re-directing the energy and force of the atrioventricular pressure gradient. The valve leaflets 22 supported by the entire valvulo-ventricular apparatus 15, 'grab onto and pull' the vortex flow directing implant 12 during systolic cycle, capturing and re-purposing the energy and force of the atrioventricular pressure gradient, and release during the diastolic cycle; this energy and force being transducted via the shaft 6, through the base plate 9, and into the structures 15 of the ventricles 19 and the ventricular free walls 17. Vortex flow directing implant 12 is further illustrated in FIG. 9.

A further function of support ring 7 of the dual force transduction annular implant 1a, 1b is to act as an annular support for the native valve annulus 14 as it is deployed near, to, on, or in proximity to the native valve annulus 14, assisting in reforming or reshaping a dysfunctional native valve annulus, to prevent further distortion, valvular regurgitation, and/or maintain a healthy native valve 18 and valve annulus 14.

Figure 9:
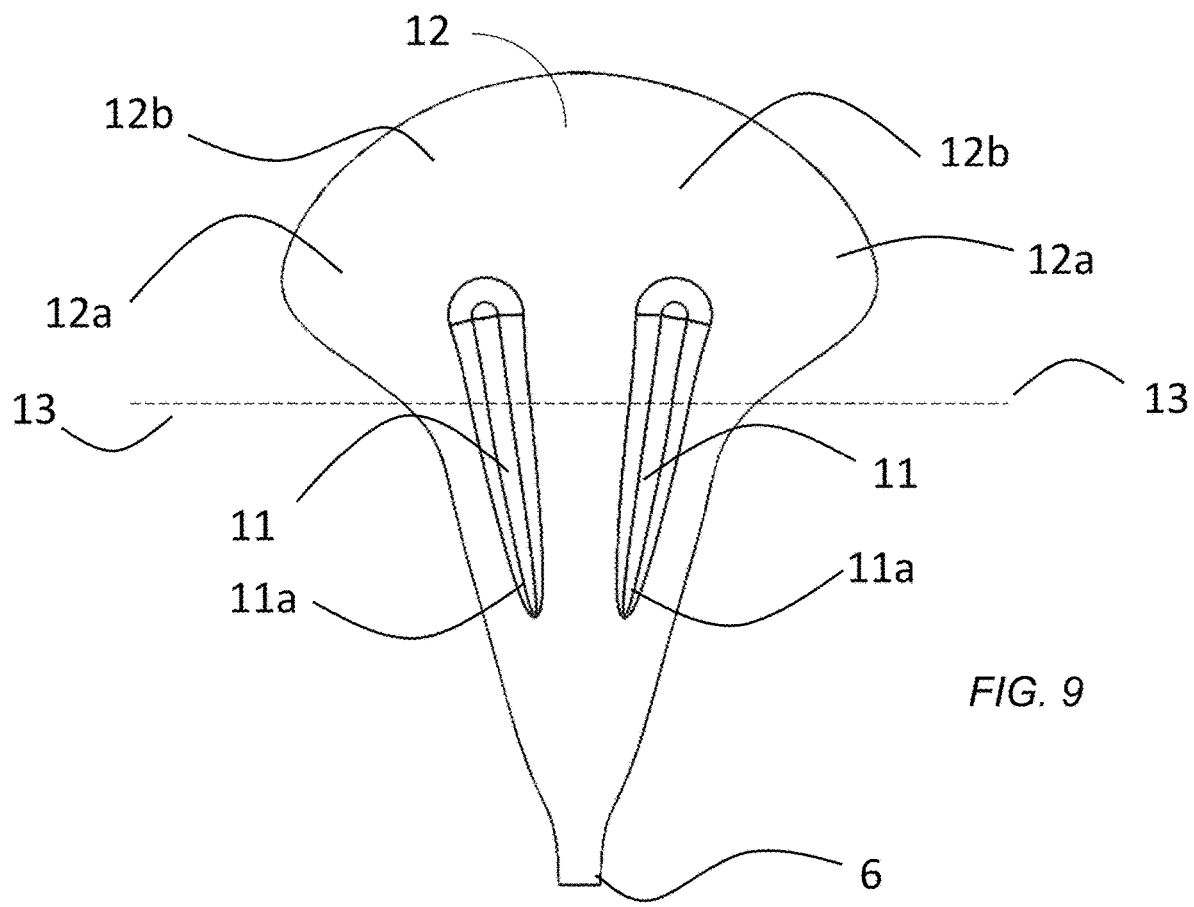
FIG. 9 is an enlarged side view of a vortex flow directing implant in accordance with an exemplary embodiment of the disclosed subject matter.

Dual force transduction annular implant 1a may include a vortex flow directing implant 12, further illustrated in FIG. 9, that captures, at the line of coaptation 13 or at the point the valve leaflets come together on the vortex flow directing implant 12, the native force of the atrioventricular pressure gradient, the valvular and subvalular structures 15, and vatrioventricular pressure gradients (e.g., the difference in the systolic pressure in the ventricle 19 and the atrium 20), as the valve leaflets 22 (See, FIG. 4), 'grab onto and pull' on the vortex flow directing implant 12 in systole. The valve leaflets 22 act on the exposed surface area in contact of the 'member' 12 as the leaflets 22 are influenced to close by the pressure differential generated by the atrioventricular pressure gradient during the ventricular systole. This action captures the energy and force conveyed by the atrioventricular pressure gradient. This captured energy and force is then moved or transducted via the shaft 6 to the base plate 9 and into the ventricular structures 15, the ventricle 19, and the ventricular free wall 17. This process results in the positive re-shaping of the ventricle called reverse remodeling.

The frame 2, its flexible cross-section struts 3, or struts transitioning into ribs 5 running parallel to the vortex flow directing implant 12 down to the atrial side 20 of the annular ring 7, at which point they transition, forming a cinching and connecting (connecting the annulus 14 to the apex 16) tether 6, resting on or in the proximity of, and/or buttressing against the atrial side annular ring 14, of the native or prosthetic valve.

The vortex flow directing implant 12 attached to the dual force transduction annular implant ring (See, FIG. 13) may be fixed in the valve 18. The dual force transduction annular implant 1a is distally fixed to the vortex flow directing implant 12 at the top of the shaft 6. The flexible structure 2 and annular ring 7 is cinched up against, buttressed to, and/or fixed to the annulus 14. During systole, the 'grab and pull' of the valve leaflets 22, the atrioventricular pressure gradient, and the muscular action, motion, energy, and contortion of the endocardium, myocardium, and epicardium are captured by the vortex flow directing implant 12 (by allowing the pressure differential to act on the exposed area of the 'member' 12) while the dual force transduction annular implant 1a releases its loaded energy and force. The elastic, spring recoil-based, and/or external energy is loaded, added, and then transferred together by the dual force transduction annular implant 1a as it presses on the annulus 14, it is now cinched, connected, and tethered to the apex, by the shaft 6 to the base plate 9, to the apex 16 of the heart 21. This, now, compounded energy and force, loading in diastole and releasing in systole, is delivered via the shaft 6 to the base plate 9 and therapeutically transferred into the structures 15, the ventricles 19, and the ventricular walls 17 thus restoring, assisting, or re-creating the valvulo-ventricular interaction a healthy ventricle experiences and requires.

The flow channel creating rib(s) 11 running at angle 11a along the surface of the vortex flow directing implant 12 directs or re-directs the intercepted flow of blood onto and off of the valve leaflets 22, and facilitates establishment a proper vector upon entry into the ventricle 19 under visualization as the vector can be altered by increasing or decreasing the 'member' 12 width or girth. This hemodynamic re-vector enhances, assists, restores (the missing), and/or enables the natural physiologic vector, thereby facilitating and/or enhancing the restoration of the ventricular vortex, critical to physiologic healthy intracardiac flow. The valvular and subvalvular structures 15, 22 'grabbing and pulling' of the vortex flow directing implant 12 (allowing the pressure differential to act on the exposed area of the 'member' 12) along with the additional elastic, spring-recoil based, and/or externally added force delivered by the dual force transduction annular implant 1 a, in effect becomes a prosthetic, or an additional, papillary muscle 23 to assist the native papillary muscles 23, replaces lost valvulo-ventricular interaction, which enables, repairs, and supports ventricular health, ventricular contraction, ventricular ejection, and assists in maintaining a healthy ventricular structure and ventricular wall structure, by transducting this captured native energy and force via the base plate 9 which then, by tether 6 to and contact with the apex 16 and ventricle 19, and utilizing specific edge shapes 9b, delivers this captured and harnessed natural energy and force into the ventricular walls 17, thereby aiding in systolic function and inducing reverse remodeling (positive geometric reshaping) of that structure 19, 21.

Dual Force Transduction Annular Implant 1b

According to a second embodiment, the dual force transduction annular implant 1b has several functions. The dual force transduction annular implant 1b is substantially identical to dual force transduction implant 1a, with the differences noted herein. In particular, dual force transduction annular implant 1b does not include the vortex flow directing implant 12. The flexible or rigid cross sectional structure 3, strut, and/or struts, transitioning into ribs 5, the ribs 5 then transitioning into a D-Frame or circular shaped, self expanding annular ring 7 conforming to an anatomical topography 14, and cinching or connecting (mechanically connecting the annulus 14 to the apex 16) to a nitinol, elastic, spring recoil-based, and/or externally added energy to the annulus 14 and/or ventricular wall 17 to aid or assist in ventricular function, during the cardiac cycle, by absorbing and loading energy during one phase, and subsequently releasing it during the next phase, absorbing and loading in one phase releasing in next phase. That energy and force is captured and loaded by distal implant and transferred via the tether or shaft 6 from the valve annulus 14 to the apex 16. This energy and force is the transducted muscular action, muscular force, and rotational energy and force of the heart, delivered by the shaft 6, to the base plate 9, which then therapeutically delivers this energy and force into the ventricular structures 15, 19 and ventricular walls 17.

This cinching and connecting (connecting the annulus 14 to the apex 16) tether or conduit 6 from the atrial 20 side of the annulus 14 to the apex 16 of the heart 21 creates an additional method or delivery of native energy and force capture by tethering between the annulus and apex thus assisting the native papillary muscles 23, delivering additional cardiac muscular energy, compounded, into the ventricular walls 17 and structures via the shaft 6, and the 'ball jointed' 9a base plate 9 during systole and diastole. The dual force transduction annular implant 1b, its structure 2,7, and ribs 5 running out and away from the fixation point 4 at the top of the shaft 4, 6, down to the atrial 20 side of the annular ring 2, at which point they transition forming a supporting ring 2, 7 resting and buttressing the attached device 2, distal to the annular ring 14, in such a manner, that during systole, the muscular motion, energy, and contortion of the endocardium, myocardium, and epicardium is captured and loaded in one phase, delivered or released in another, and this energy and force delivered via the shaft 6 to the 'ball jointed' 9a base plate 9 and therapeutically transferred 9, 9b into the ventricle 19, the ventricular structures and ventricular walls 17.

Another function of ring 7 of dual force transduction annular implant 1b is to act as an annular support ring for the valve annulus 14 as it is deployed near, to, on, or in proximity to the valve annulus 14 assisting in reforming or re-shaping a dysfunctional valve annulus 14.

The dual force transduction implant 1b may be fixed to an axially or longitudinally adjustable shaft 6, which may increase the force by moving the shaft 6 proximally, thereby increasing the pressure of the connection 14 between the annular ring 7 and the apex 16 of the heart, or decrease the force by moving the shaft 6 distally thereby decreasing the pressure of the connection between the annular ring 14 and the apex 16 of the heart. The energy and force delivery occurs via the conduit or shaft 6 to the base plate 9, which then transfers the energy and force into the ventricular structures 15, 17, 19. In cinching the annulus 14 to the apex 16, the energy and force loaded in the diastolic phase and released in the systolic phase can be adjusted by moving the tether or shaft 6 distally for less added force or proximally for more added force.

The fixed, 'ball jointed' 9a base plate 9, with round oval cutouts 9c to allow fibrous tissue in-growth for long term security, pulls the apex 16 upward in systole and releases the apex 16 in diastole and, in conjunction with the elongated therapeutic extensions 9b of the base 9 plate extending up the sides of the ventricle 9b, impart by contact, specific shape, and fixation this transducted energy into the ventricle 19, inducing a physiologic response by replacing the lost valvulo-ventricular interaction, which critically supports ventricular contraction and assists in maintaining a healthy ventricular wall structure, required to maintain healthy geometric ventricular 19 shape.

The control unit 10, illustrated in FIG. 10, above, may be used with either dual force transduction implant 1a or 1b or the vortex flow directing implant 12 and have three or more independent contained chambers 10b, 10c, 10d, each identifiable below the skin by palpable protrusions, one palpable protrusion for chamber one 10b, two palpable protrusions for chamber two 10c, and three palpable protrusions for chamber three 10d. A single connection point 10a places the control unit 10 in communication, via the connecting multi-lumen tubing 8 and shaft 6, with the vortex flow directing implant 12, and has a needle access pad of ePTFE, any semi-porous, or non-porous material, that allows fibrous tissue in growth (the body's method of preventing infection and facilitating hemostasis). Additional compartments may be added to house, store, and/or accommodate additional sensing equipment, power sources, data transmission equipment, or the sensors themselves.

Figure 10:
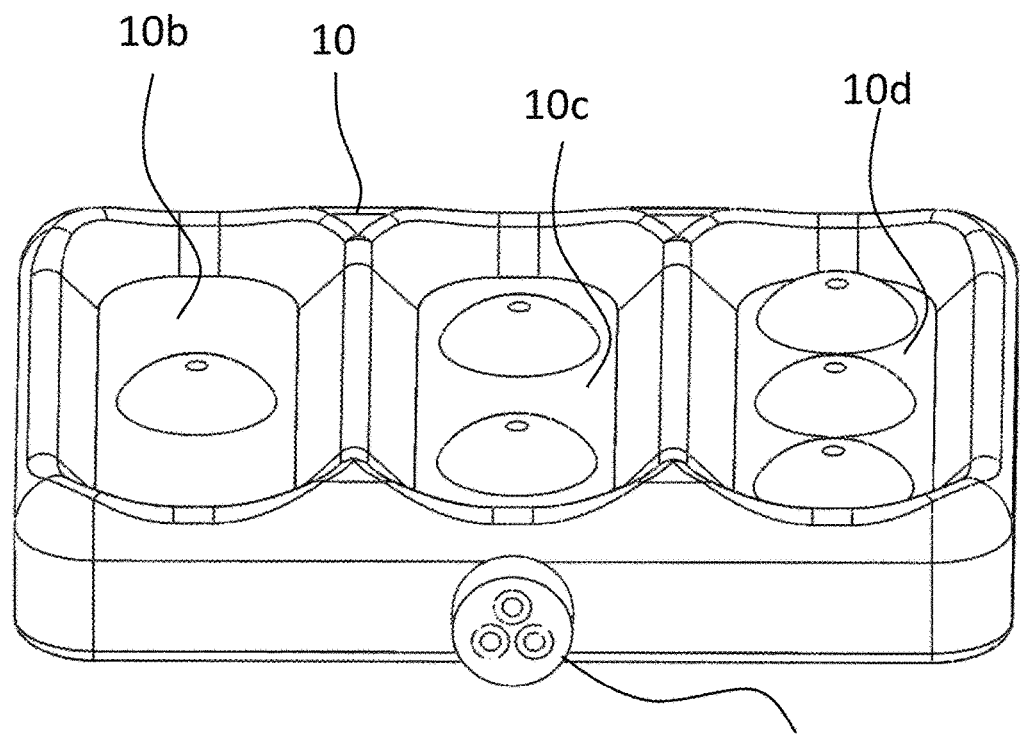
FIG. 10 is an enlarged perspective view of a control unit in accordance with an exemplary embodiment of the disclosed subject matter.
Figure 11:
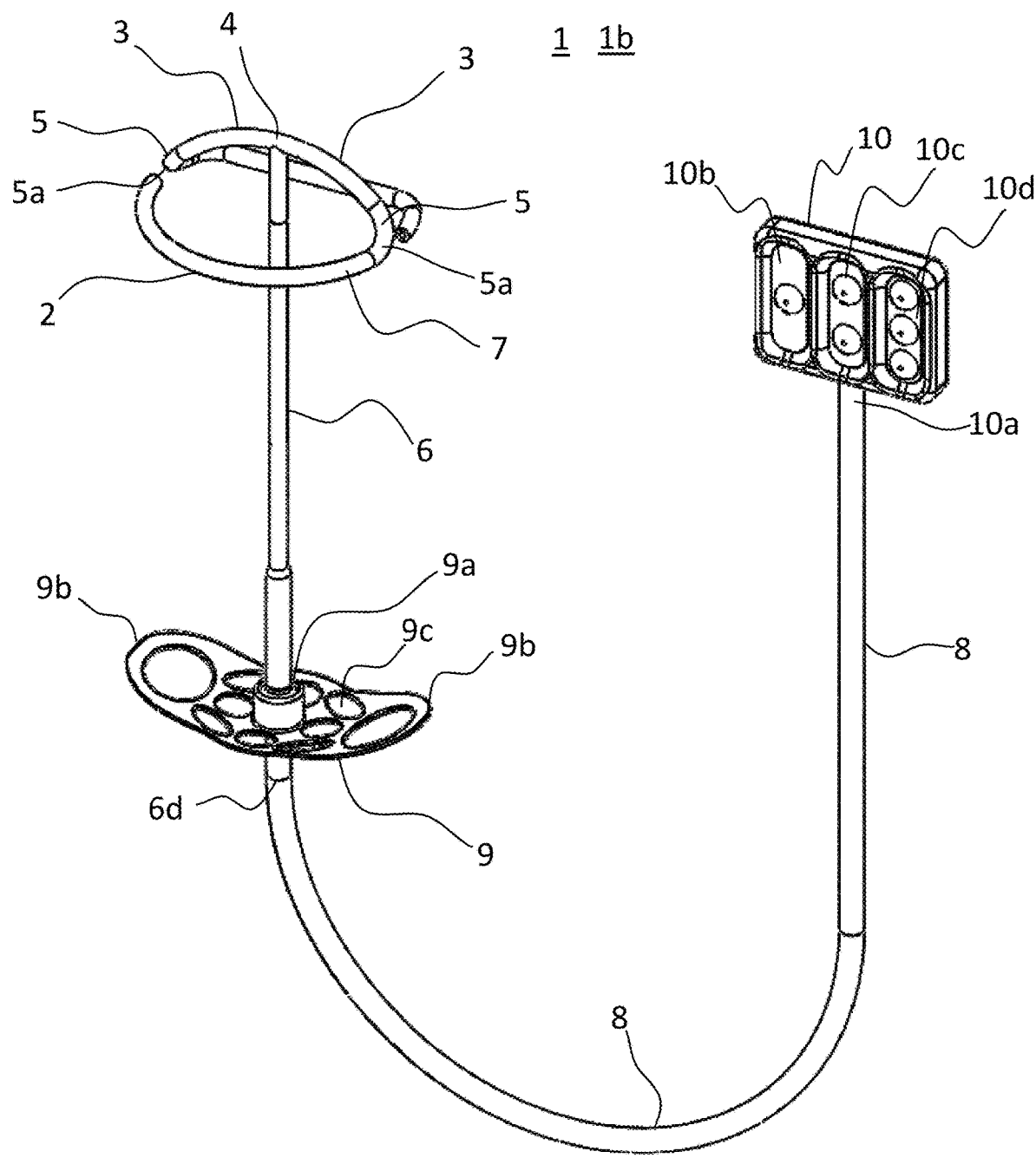
FIG. 11 is a perspective view of an implant system in accordance with a second exemplary embodiment of the disclosed subject matter.
Figure 12:
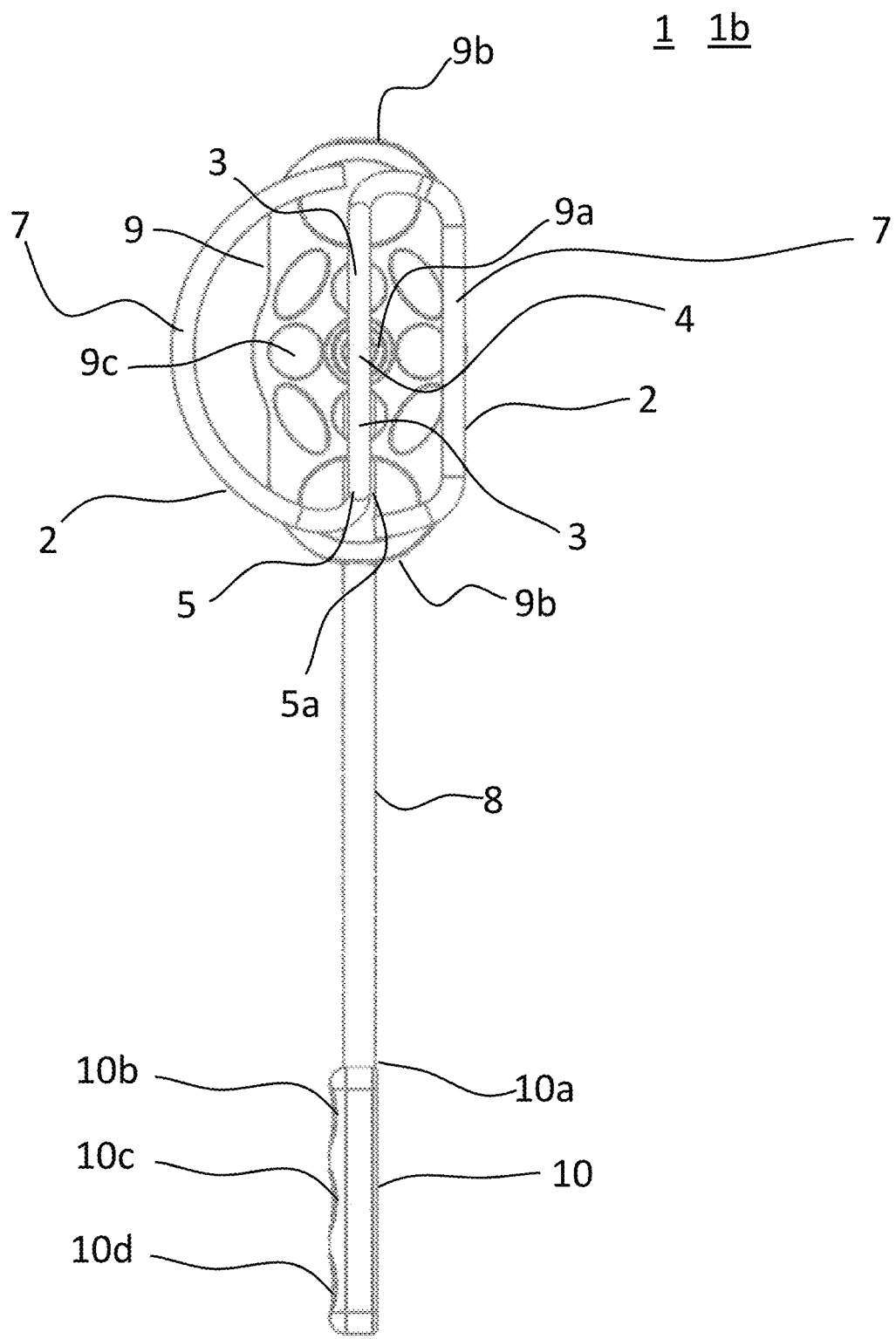
FIG. 12 is a top view of an implant system in accordance with a second exemplary embodiment of the disclosed subject matter.

By reference to FIGS. 9 and 10, in one of chambers 10b 10c 10d, a sealed compartment is introduced to house a power source for sensing nodes implanted within the device 1a, 1b itself, the implant system 1 then becoming a housing platform for these sensing nodes. One or more lumens of the connecting multi-lumen connecting tube 8 may be used to connect the power source with the sensing nodes. In one of chambers 10b 10c 10d, fluid is introduced or removed from the integrated inflatable axial adjusting balloon 6a to increase or decrease the axial positioning shaft 6 of the vortex flow directing implant 12 as reverse re-modeling occurs. In one of chambers 10b 10c 10d, fluid is added to increase or decrease the girth of the vortex flow directing implant 12. In one of chambers 10b 10c 10d, fluid is added or removed to create crescent shaped articulation 12b in the wings 12a of vortex flow directing implant 12, either anterior or posterior, to better vector the intercept of blood from atrium 12 by introducing fluid into the 'wing' chambers 12a via a skeletal crescent beam with lumen (not shown).

Figure 15:
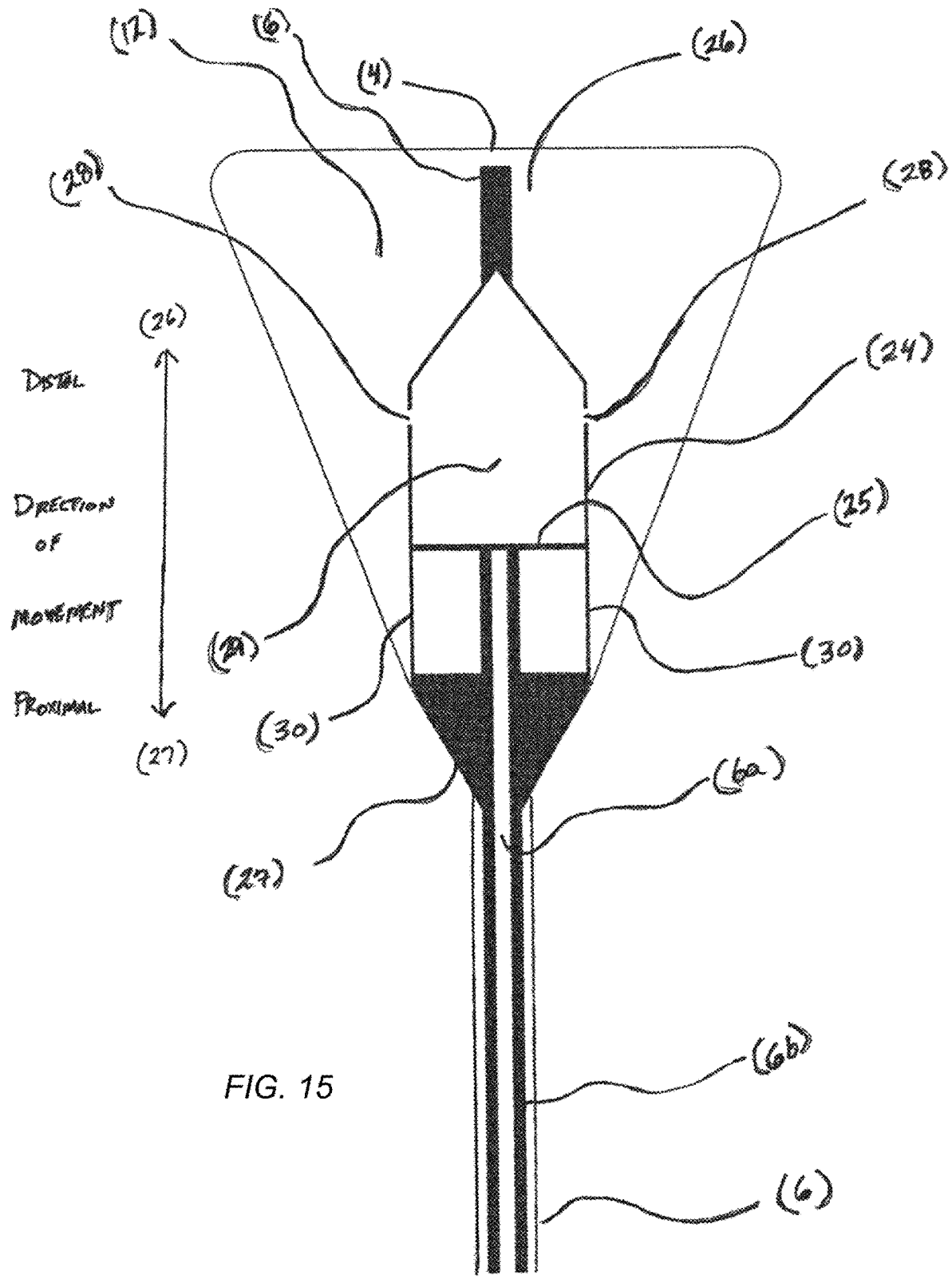
FIG. 15 is a cross-sectional view of an adjustment assembly in accordance with exemplary embodiments of the disclosed subject matter.

With continued reference to the first embodiment, FIG. 15 illustrates a novel piston 25 fixed to the moving portion 6b of the shaft 6 within a cylinder 24 fixed to said shaft 6. The piston 25 may be contained within the shaft 6 and/or within the vortex flow directing implant 12 that allows the sliding shaft 6a, the vortex flow directing implant 12 and the cylinder 24, to axially or longitudinally move up (arrow 26) and down (arrow 27) as the fluid in the vortex flow directing implant 12, powered by the atrioventricular pressure gradient, rises and falls as the heart naturally cycles through diastole and systole.

During diastole, the fluid contained within the vortex flow directing implant 12 moves proximally (arrow 27, forced by the pressure differential and/or the hemodynamic in flow to the bottom portion of the vortex flow directing implant 12 and then, conversely, rises distally (arrow 26), under pressured force to the distal 26 end of the vortex flow directing implant 12, during systole thereby causing the fluid contained within the vortex flow directing implant 12 to move with an energy and force and fill the distal portion of the vortex flow directing implant 12. The cylinder 24, via the two side positioned fill holes 28, is then filled by fluid, under pressure and force, and drives the piston 25 proximally (arrow 27). This novel cylinder 24 is housed within the inflatable vortex flow directing implant 12 and fixed to the distal end of the vortex flow directing implant 12 by the shaft 6 at the central fixation point 4. The piston 25 moves independently within the cylinder 24 and is driven proximally (arrow 27) (a) by fluid filling the 'piston chamber bowl' 29 under pressure, via the two side positioned cylinder fill holes 28, (b) by the fluid influenced and powered by the native systolic forces. The piston 25 moves the entire vortex flow directing implant 12 distally (arrow 26), thereby creating a new, additional, and/or redirected energy and force, from the fluid's distal/proximal exchange (arrow 26/arrow 27), during the heart's cycle.

In an exemplary embodiment, a fluid exchange system is provided by piston 25, which is operated and/or natively 'powered' (by the atrioventricular pressure gradient during the systolic cycle) and is a therapeutic component being driven by the heart's natural energy and force, generated, captured by vortex flow directing implant 12 and redirected by shaft 6, delivered in a therapeutic manner, during natural diastole and systole utilizing the fluid contained and driven within the vortex flow directing implant 12. The movement of the fluid housed within the vortex flow directing implant 12, being driven to the distal end 26 of the vortex flow directing implant 12 during the systolic cycle, forces fluid into the cylinder fill holes 28, located on each side of the cylinder 24, and fills the piston chamber bowl 29 in the systolic cycle, and pressurizes the chamber (29) (arrow 26), thereby moving the piston contained within the vortex flow directing implant 12 distally (arrow 26), in the heart's cycle, generating a re-directed therapeutic force when transducted and/or delivered to the ventricular structures 15, 17, 19 and ventricular free walls 17. The cylinder 24, fixed to the implant 4 and the vortex flow directing implant 12, in systole, raises the vortex flow directing implant 12 distally (arrow 26), and conversely, in diastole, reverses the action (arrow 27). The vortex flow directing implant 12 now becomes a 'pumping piston,' delivering an additional energy and force augmenting the valvulo-ventricular interaction 15, an in effect becomes an additional papillary muscle 23, delivering native energy and force, via the conduit or shaft 6 and via the base plate 9, into the ventricular structure 19 and/or the ventricular free walls 17. Conversely, by lowering the cylinder side fill holes 28 to a position 30 below the piston 25, the reverse is achieved, e.g., in diastole the piston 25 is driven distally (arrow 26), the vortex flow directing implant 12 now moves proximally (arrow 27), and in systole the piston 25 is driven proximally (arrow 27), the vortex flow directing implant 12 now moving distally (arrow 26).

It will be appreciated that the methods and systems described above are set forth by way of example and not of limitation. Numerous variations, additions, omissions, and other modifications will be apparent to one of ordinary skill in the art. Thus, while particular embodiments have been shown and described, it will be apparent to those skilled in the art that various changes and modifications in form and details may be made therein without departing from the spirit and scope of this disclosure and are intended to form a part of the disclosure as defined by the following claims, which are to be interpreted in the broadest sense allowable by law.

What is claimed is:

1. An implant system for restoring ventricular geometric shape and changing vortical physiological intracardiac flow in a human heart, the implant system comprising:
    an annular implant comprising laterally extending struts transitioning into annular structural components for positioning the implant and transducting force on an atrial side of a valve annulus of a native valve;
    an anchoring system comprising one or more base plate assemblies attachable to an apex or wall of the heart;
    a tether assembly comprising a shaft connected between the implant and the one or more base plate assemblies;
    a conduit providing a fluidic connection; and
    a control unit.

2. The implant system of claim 1, wherein the implant further comprises a bladder configured for altering cardiac flow, altering hemodynamic vector, or altering intracardiac vortical formation or flow.

3. The implant system of claim 1, wherein the implant further comprises a bladder configured for capturing atrio-ventricular pressure gradient energy and force and transducting the energy and the force to the shaft.

4. The implant system of claim 1, wherein the implant further comprises a bladder having a predefined shape, the bladder being fixed on the shaft and configured for altering cardiac and ventricular inflow velocity and volume.

5. The implant system of claim 1, wherein the annular implant is configured as a force-transducting structure and an intracardiac supporting structural scaffold fixed at an inflow side of the shaft in an atrium of the heart thereby mechanically tethering the native valve and valvular apparatus to the apex of the human heart.

6. The implant system of claim 1, wherein the annular structural components are configured to contact a valve annular structure of the heart.

7. The implant system of claim 1, wherein the annular structural components are adapted to stabilize the device, center the device, bias the device, or transduct force to and into an annulus, a ventricle, and one or more ventricular structures and aid in the formation of proper vortical flow and proper ventricular function and ejection.

8. The implant system of claim 1, wherein the annular structural components are fixed and in contact with a valve annular structure, and shape or re-shape a valve annular structure, a ventricle, and one or more ventricular structures.

9. The implant system of claim 1, wherein the laterally extending struts are nitinol and/or elastic in property and/or spring-based to absorb, store, recoil, or transfer energy.

10. The implant system of claim 1, wherein the laterally extending struts capture and load in one phase and release in the subsequent phase, wherein the struts comprise nitinol, an elastic material or a spring to transduct native cardiac energy and force via the shaft to the one or more base plate assemblies.

11. The implant system of claim 1, wherein the implant system is used to set a tension to expand or contract the distance from a valve annulus to an apex distance.

12. The implant system of claim 1, wherein the annular implant comprises one or more anchoring points configured to anchor the implant in the human heart.

13. The implant system of claim 1, wherein the annular structural components are configured to be positioned on an inflow side of the valve.

14. The implant system of claim 1, wherein the annular structural components are expandable.

15. The implant system of claim 1, wherein the annular structural components comprise a covering material configured to promote endothelization and ingrowth to native tissue.

16. The implant system of claim 1, further comprising a vortex flow directing member, wherein the annular implant is coupled to the vortex flow directing member.

17. The implant system of claim 1, wherein the annular implant is detachable from the vortex flow directing member.

18. The implant system of claim 1, wherein the annular structural components alter a shape of the valve annulus.

19. The implant system of claim 1, wherein the annular structural components are configured to control a shape of the valve annulus of the heart thereby providing a frame for geometric restoration.

20. The implant system of claim 1, wherein the annular structural components define a D-shape, a saddle shape, a circular shape, or oval shape.

21. The implant system of claim 1, wherein the annular implant is self-expanding.

22. The implant system of claim 1, wherein the annular implant transducts atrio-valvulo energy and force into one or more ventricular structures.

23. The implant system of claim 1, further comprising a vortex flow directing member, wherein the vortex flow directing member comprises a shape configured to vector hemodynamic flow and capture native cardiac energy and force.

24. The implant system of claim 23, wherein the vortex flow directing member is an additional component of the annular implant.

25. The implant system of claim 23, wherein the vortex flow directing member comprises one or more surfaces that function as a sealing surface for one or more valve leaflets of the native valve.

26. The implant system of claim 23, wherein the vortex flow directing member is filled with a fluid, gas, solid or gel.

27. The implant system of claim 23, wherein the annular structural components are detachable from the vortex flow directing member and the shaft.

28. The implant system of claim 23, wherein the annular structural components are coupled to the vortex flow directing member.

29. The implant system of claim 23, wherein the vortex flow directing member comprises an adjustable surface for altering hemodynamic flow having a planer, convex, or concave shape, wherein the shape of the adjustable surface is configured to be altered by increasing or decreasing a volume of a fluid in a bladder to influence hemodynamic flow.

30. The implant system of claim 29, wherein the vortex flow directing member is configured to be adjusted by increasing or decreasing fluid level within the bladder.

31. The implant system of claim 29, wherein the vortex flow directing member is configured to be situated partially in and atrium and partially in a ventricle to alter incoming ventricular blood flow with the adjustable surface.

32. The implant system of claim 23, wherein the vortex flow directing member comprises a fluidic adjustment connection to the control unit.

33. The implant system of claim 23, wherein the annular implant is configured to tether the valve annulus to the apex of the heart via the shaft to aid in ventricular motion by absorbing energy during a cardiac cycle, and subsequently releasing said energy during a next phase of the cardiac cycle.

34. The implant system of claim 23, wherein the vortex flow directing member comprises lateral struts configured to alter hemodynamic flow out of an atrium and into a ventricle.

35. The implant system of claim 34, wherein the lateral struts comprise a coating or a wrapping utilized for endothelization and fibrous tissue in-growth.

36. The implant system of claim 34, wherein the lateral struts are configured to direct blood flowing into the ventricle to restore ventricular vortex formation.

37. The implant system of claim 34, wherein the lateral struts are configured to transfer force to and from either the vortex flow directing member or the tether assembly.

38. The implant system of claim 34, wherein the lateral struts are connected to a central shaft.

39. The implant system of claim 23, wherein the vortex flow directing member and the annular implant are adapted to capture native energy and force from one area within the human heart, redirect the energy and force to another area of the human heart, and deliver the energy and force as a therapy, a corrective measure, or a reparative action to restore a ventricle into functioning order.

40. The implant system of claim 23, wherein the vortex flow directing member is configured to capture cardiac energy and to transfer said energy into one or more ventricular structures.

41. The implant system of claim 23, wherein the control unit comprises a fluidic connection with the shaft and the vortex flow directing member.

42. The implant system of claim 23, wherein the annular implant in conjunction with the vortex flow directing member is configured to apply a force to the valve annulus to adjust a ventricular structure.

43. The implant system of claim 1, wherein the annular implant comprises one or more fixation points configured to attach to the endocardium, myocardium, or epicardium of the heart.

44. The implant system claim 1, wherein the annular implant comprises one or more annular support structures configured to be positioned at an inflow or an outflow side of the native valve.

45. The implant system of claim 1, wherein the annular implant is configured to capture native cardiac energy and force and transduct the force to other structures of the human heart by connecting a valve plane to the apex of said heart.

46. The implant system of claim 1, wherein the annular implant is configured to reduce valvular regurgitation by connection of the valve annulus to the apex of the human heart.

47. The implant system of claim 1, wherein the annular implant is tethered inside the heart in one and or more locations.

48. The implant system of claim 1, wherein the shaft comprises a polyfilament.

49. The implant system of claim 1, wherein the annular implant comprises one or more structures configured for anchoring into endocardium, myocardium, or epicardium.

50. The implant system of claim 1, wherein the shaft comprises a base plate.

51. The implant system of claim 1, wherein the base plate comprises at least one anchor selected from the group consisting of: hooks, barbs, suture, needles, suction, pledget, glue, adhesion, friction, natural ingrowth, and clamping.

52. The implant system of claim 1, further comprising an anti-thrombotic coating.

53. The implant system of claim 1, wherein the annular implant comprises at least one anchor selected from the group consisting of: hooks, barbs, suture, needles, suction, pledget, glue, adhesion, friction, ingrowth and/or clamping.

54. The implant system of claim 1, wherein the shaft comprises multi-lumen tubing.

55. The implant system of claim 1, wherein the implant system is configured to eliminate cascading effects of ventricular distortion.

56. The implant system of claim 1, wherein the annular implant comprises an elastic connection with the valve annulus and valve itself.

57. The implant system of claim 1, wherein the control unit comprises a fluid reservoir.

58. The implant system of claim 1, wherein the control unit is configured for subcutaneous implantation.

59. The implant system of claim 1, wherein the shaft is anchored to the apex of the human heart.

60. The implant system of claim 1, wherein the annular implant is configured for positioning on the atrial side of a native or prosthetic valve.

61. The implant system of claim 1, wherein the annular implant comprises a material with memory as to be a first shape for delivery and a second shape when released.

62. The implant system of claim 1, wherein the annular implant is flexible, self-expanding, and maintains memory structured to be delivered through a catheter.

63. The implant system of claim 1, wherein the annular implant comprises folding points to minimize its size while being delivered.

64. The implant system of claim 1, wherein the annular implant comprises a central support connected to two struts covered in a material to promote endothealization and ingrowth.

65. The implant system of claim 1, wherein the annular implant comprises detachable struts.

66. The implant system of claim 1, wherein the annular implant is configured to release one or more of the annular structural components with a twisting motion.

67. The implant system of claim 1, wherein the annular implant is configured to shape the annulus by increasing or decreasing circumferential tension related to increased or decreased tension on the central shaft.

68. The implant system of claim 66, wherein the annular implant is configured to be removable from the heart after releasing the one or more annular structural components.

69. The implant system of claim 1, wherein the annular implant, in conjunction with the one or more base plate assemblies, is configured to increase or decrease the applied force to the valve annulus to maintain healthy ventricular shape.

70. The implant system of claim 1, wherein the shaft is adjustable in length to thereby adjust an amount of force that is harnessed.

71. The implant system of claim 1, wherein the annular structural components are configured to remain as a permanent implant after the annular implant and shaft are removed.

72. The implant system of claim 1, further comprising an adjustment assembly comprising a piston attached to the shaft, wherein the piston is moveable within a body defining a fluid reservoir on each side of the piston.

73. The implant system of claim 72, wherein the fluid reservoirs are in external communication.

74. The implant system of claim 72, wherein the fluid reservoirs are in internal communication.

75. The implant system of claim 72, wherein the piston comprises a sealing member, and wherein the piston and the body are contained within an anchoring device.

76. The implant system of claim 72, wherein the body is disposed inside an inflatable member or balloon and the piston is contained within.

77. The implant system of claim 72, wherein the one or more base plate assemblies further includes an apical piston.

78. The implant system of claim 72, wherein the piston is coupled to the shaft and is capable of moving the shaft.

79. The implant system of claim 72, wherein a change in the amount of fluid in either reservoir adjusts a location of the piston in the body.

80. The implant system of claim 72, wherein the piston is housed within an anchoring device.

81. The implant system of claim 72, further comprising a vortex flow directing member, wherein the vortex flow directing member is fixed to the shaft.

82. The implant system of claim 81, wherein the piston is configured to increase or decrease a force applied by the vortex flow directing member.

83. The implant system of claim 81, wherein the piston is configured to open, deploy, or actuate the vortex flow directing member.

84. The implant system of claim 81, wherein the vortex flow directing member is configured to mitigate ventricular pressure loss.

85. The implant system of claim 81, wherein the piston is configured to use atrioventricular pressure gradient, rotational motion, the natural twisting of the heart, and the heart cycle to fill the vortex flow directing member.

86. The implant system of claim 72, wherein the piston is configured to transfer valvular energy and force to the shaft.

87. The implant system of claim 72, wherein the piston is configured to be logitudinally adjusted by changing a volume of fluid in the fluid reservoir to thereby move the piston and shaft laterally or longitudinally.

88. The implant system of claim 72, wherein the piston is configured to move the annular implant within between valve leaflets.

89. The implant system of claim 72, wherein the piston is configured to move the annular implant to thereby alter a vector at which blood flows off of leaflets of the native valve.

90. The implant system of claim 72, wherein the piston is configured to move the annular implant to thereby amplify a force applied to a heart structure.

91. The implant system of claim 72, wherein the piston comprises two or more independently adjustable valves for compression and rebound adjustment.

92. The implant system of claim 72, wherein the piston allows for up to and including 360 degrees of rotation.

93. The implant system of claim 72, further comprising external fluid conducting tubing and wherein the control unit is disposed external to a human body, and wherein the piston is actuated by a hydraulic force via a hydraulic cylinder.

94. The implant system of claim 93, wherein the hydraulic cylinder is disposed within the one or more base plate assemblies.

95. The implant system of claim 72, wherein the adjustment assembly comprises two pistons, wherein each piston comprises a shaft and a reservoir between them.

96. The implant system of claim 72, wherein the shaft comprises a moveable section and a stationary section, wherein the moveable section is attached to the piston.

97. The implant system of claim 72, wherein the piston is configured to alter flow vectors across valvular leaflets to thereby restore healthy physiologic intracardiac flow.

98. The implant system of claim 72, wherein the piston is configured to enhance atrioventricular pressure gradient energy and force.

99. The implant system of claim 72, wherein the piston is configured to close, retract, or de-activate the vortex flow directing member.

100. The implant system of claim 72, wherein the piston comprises a cylinder having a spiral shape, wherein the piston is keyed into the spiral shape.

101. The implant system of claim 72, wherein the anchoring system is configured to be affixed to the apex of the human heart.

102. The implant system of claim 72, wherein the piston is contained in the vortex flow directing member.

103. The implant system of claim 72, wherein the piston is configured to use native hemodynamic pressure for adjustment.

104. The implant system of claim 72, wherein the control unit is configured to adjust the volume in the piston.

105. The implant system of claim 1, wherein the shaft is pressure adjustable.

106. The implant system of claim 1, wherein the control unit comprises one or more needle-pierceable sealed sections.

107. The implant system of claim 1, wherein the control unit comprises a rigid back to prevent puncturing via a needle through the back.

108. The implant system of claim 1, wherein the control unit comprises one or more separate fluid chambers.

109. The implant system of claim 1, wherein the control unit comprises a fluid connection.

110. The implant system of claim 1, wherein the control unit compartments are configured to be individually identified via palpitation.

111. The implant system of claim 1, wherein the control unit comprises radiopaque markers.

* * * * *